United States Patent [19]
Uchida et al.

[11] Patent Number: 5,928,638
[45] Date of Patent: Jul. 27, 1999

[54] METHODS FOR GENE TRANSFER

[75] Inventors: Nobuko Uchida, Palo Alto; Ann Tsukamoto, Portola Valley; Irving Weissman, Redwood City, all of Calif.

[73] Assignee: SyStemix, Inc., Palo Alto, Calif.

[21] Appl. No.: 08/664,358

[22] Filed: Jun. 17, 1996

[51] Int. Cl.$^6$ .................................................. A01N 63/00
[52] U.S. Cl. .................. 424/93.21; 435/69.1; 435/320.1; 435/325; 530/389.6; 514/44; 424/529
[58] Field of Search ................................ 424/93.21, 520, 424/529; 514/44; 530/389.6; 935/59, 16, 52; 435/325, 455, 69.1, 320.1

[56] References Cited

U.S. PATENT DOCUMENTS

| | | |
|---|---|---|
| 5,035,994 | 7/1991 | Civin . |
| 5,061,620 | 10/1991 | Tsukamoto et al. . |
| 5,409,813 | 4/1995 | Schwartz . |
| 5,449,614 | 9/1995 | Danos et al. . |
| 5,489,516 | 2/1996 | Broudy et al. . |
| 5,604,090 | 2/1997 | Alexander et al. .......................... 435/5 |
| 5,604,900 | 2/1997 | Alexander et al. .......................... 435/5 |

FOREIGN PATENT DOCUMENTS

| | | |
|---|---|---|
| 2 086 844 | 7/1994 | Canada . |
| 0 662 512 | 7/1995 | European Pat. Off. . |
| WO 92/05266 | 4/1992 | WIPO . |
| WO 92/14829 | 9/1992 | WIPO . |
| WO 93/09792 | 5/1993 | WIPO . |
| WO 93/14188 | 7/1993 | WIPO . |
| 93 19660 | 10/1993 | WIPO . |
| WO 94/02016 | 2/1994 | WIPO . |
| WO 94/09363 | 4/1994 | WIPO . |
| WO 94/11027 | 5/1994 | WIPO . |
| WO 94/11524 | 5/1994 | WIPO . |
| WO 94/29438 | 12/1994 | WIPO . |
| WO 95/05843 | 3/1995 | WIPO . |
| WO 95/09912 | 4/1995 | WIPO . |
| WO 95/12317 | 5/1995 | WIPO . |
| WO 95/15167 | 6/1995 | WIPO . |
| WO 95/19793 | 7/1995 | WIPO . |
| 95 33824 | 12/1995 | WIPO . |
| 96 09400 | 3/1996 | WIPO . |

OTHER PUBLICATIONS

Herrman. J. Mol. Med. Today. 1995, 73:157–163.
Ronald Crystal. Science. 1995, 270:404–409.
Stefan Karlsson. Blood. 1991, vol. 87, No. 10:2481–2491.
Banerjee et al. Stem Cells. 1994, 12/4, p. 380.
Lord et al. Stem Cells. 1993, 11:212–217.
Takahashi et al. Exp. Hematol. 1991, 19:343–346.
Russell et al. P.N.A.S. Jun. 6, 1995, vol. 92, pp. 5719–5723).
Culver et al. TIG. 1994, vol. 10, No. 5:175–178.
Coghlan. New Scientist. 1995.
Orkin and Motulsky, NIH Report on Gene Therapy. 1995.
Gordon et al., "Routes to repopulation—a unification of the stochastic model and separation of stem–cell subpopulations" *Leukemia* (1994) 8:1068–1073.

Reddy et al., "Approaches to synchronize murine bone marrow cells at various stages in cell cycle" *Exp. Hematol.* (1995) 23:813. (Abstract 248).
Peters et al., "Murine marrow cells expanded in culture with IL–3, IL–6, IL–11, and SCF acquire an engraftment defect in normal hosts" *Exp. Hematol.* (1995) 23:461–469.
Skønsberg et al., "Interleukin–7 differentiates a subgroup of acute lymphoblastic leukemias" *Blood* (1991) 77:2445–2450.
Kittler et al., Enhancement of retroviral integration by cytokine stimulation impairs engraftment of bone marrow cells into non–myeloablated hosts *Blood* (1994) 84:344A. (Abstract 1360).
Bodine et al., "Survival and retrovirus infection of murine hematopoietic stem cells in vitro: Effects of 5–FU and method of infection" *Exp. Hematol.* (1991) 19:206–212.
Paukovits et al., "The myelostimulatory dekapeptide (pEEDCK)$_2$ induces proliferation in pluripotent hemopoietic stem cells in vivo and increases leukocyte and platelet production: A possible alternative for recombinant hemopoietic growth factors" *Cancer Research Therapy & Control* (1995) 4:203–209.
Timson, "Hydroxyurea" *Mut. Res.* (1975) 32:115–132.
Eriksson et al., "Deoxyribonucleoside triphosphate metabolism and the mammalian cell cycle" *Exp. Cell. Res.* (1987) 168:79–88.
Morse et al., "The effect of hydroxyurea on differentiated marrow erythroid precursors" *Proc. Soc. Exp. Biol. Med.* (1969) 130:986–989.
Bhuyan et al., "Cell–kill kinetics of several S–phase–specific drugs" *Cancer Res.* (1973) 33:888–894.
Kennedy, "The evolution of hydroxyurea therapy in chronic myelogenous leukemia" *Seminars in Oncology* (1992) 19:21–26.
Terstappen et al., "Flow cytometric assessment of human T–cell differentiation in thymus and bone marrow" *Blood* (1992) 79:666–677.
Issaragrisil et al., "Brief report: Transplantation of cord––blood stem cells into a patient with severe thalassemia" *N. Engl. J. Med.* (1995) 332:367–369.
Yau et al., "Purging of T–lymphocytes with magnetic affinity colloid" *Exp. Hematol.* (1990) 18:219–222.
Takaue, "Depletion of T lymphocytes from human bone marrow by the use of counterflow elutriation centrifugation" *Am. J. Hematol.* (1986) 23:247–262.

(List continued on next page.)

*Primary Examiner*—Bruce R. Campell
*Assistant Examiner*—Dave Trong Nguyen
*Attorney, Agent, or Firm*—Melissa A. Shaw

[57] ABSTRACT

The present invention provides a method for optimizing gene transfer into hematopoietic stem cells (HSCs) by contacting the cells with hydroxyurea prior to gene transfer to induce HSCs in G0 into active cell cycle. This method is useful for treating patients suffering from a disease that is suitably treated by gene therapy or involves hematopoietic cells. A method is also provided for enhancing the efficacy of bone marrow transplantation by administering hydroxyurea to increase HSC yields.

9 Claims, 10 Drawing Sheets

OTHER PUBLICATIONS

Charache et al., "Effect of hydroxyurea on the frequency of painful crises in sickle cell anemia" *N. Eng. J. Med.* (1995) 332:1317–1322.

Veale et al., "Phase 1 study of high–dose hydroxyurea in lung cancer" *Chemother. Pharmacol.* (1988) 21:53–56.

Vichinsky et al., "A cautionary note regarding hydroxyurea in sickle cell disease" *Blood* (1994) 83:1124–1128.

Miller et al., "Generation of helper–free amphotropic retroviruses that transduce a dominant–acting, methotrexate–resistant dihydrofolate reductase gene" *Mol. Cell. Biol.* (1985) 5:431–437.

Miller et al., "Redesign of retrovirus packaging cell lines to avoid recombination leading to helper virus production" *Mol. Cell. Biol.* (1986) 6:2895–2902.

Danos et al., "Safe and efficient generation of recombinant retroviruses with amphotropic and ecotropic host ranges" *Proc. Natl. Acad. Sci. USA* (1988) 85:6460–6464.

Burns et al., "Vesicular stomatitis virus G glycoprotein pseudotyped retroviral vectors: Concentration to very high titer and efficient gene transfer into mammalian and non-mammalian cells" *Proc. Natl. Acad. Sci USA* (1993) 90:8033–8037.

Kasahara et al., "Tissue–specific targeting of retroviral vectors through ligand–receptor interactions" *Science* (1994) 266:1373–1376.

Ohashi et al., "Efficient transfer and sustained high expression of the human glucocerebrosidase gene in mice and their functional macrophages following transplantation of bone marrow transduced by a retroviral vector" *Proc. Natl. Acad. Sci.* (1992) 89:11332–11336.

Correll et al., "High levels of human glucocerebrosidase activity in macrophages of long–term reconstituted mice after retroviral infection of hematopoietic stem cells" *Blood* (1992) 80:331–336.

Mullen et al., "Transfer of the bacterial gene for cytosine deaminase to mammalian cells confers lethal sensitivity to 5–fluorocytosine: A negative selection system" *Proc. Natl. Acad. Sci. USA* (1992) 89:33–37.

To et al., "Inhibition of retroviral replication by anti–sense RNA" *Mol. Cell. Biol.* (1986) 6:4758–4762.

Hopper et al., "Inhibition of retroviral replication by antisense RNA expression" *Current Communications in Biology, Viral Vectors* (1988) Gluzman and Hughes (eds.), Cold Spring Harbor Laboratory, Cold Spring Harbor, NY. pp. 139–145.

Rhodes et al., "Inhibition of heterologous strains of HIV by antisense RNA" *AIDS* (1991) 5:145–151.

von Rüden et al., "Inhibition of human T–cell leukemia virus type I replication in primary himan T cells that express antisense RNA" *J. Virol.* (1989) 63:677–682.

Morse III et al., "Genetic nomenclature for loci controlling mouse lymphocyte antigens" *Immunogenetics* (1987) 25:71–78.

Spangrude et al., "Purification and characterization of mouse hematopoietic stem cells" *Science* (1988) 241:58–61.

Uchida, "Characterization of mouse hematopoietic stem cells" *Ph.D. Thesis* (1992) Stanford University.

Brenner, "Gene transfer into human hematopoietic progenitor cells: A review of current clinical protocols" *J. Hematotherapy* (1993) 2:7–17.

Charache et al., "Hydroxyurea–induced augmentation of fetal hemoglobin production in patients with sickle cell anemia" *Blood* (1987) 69:109–116.

Goldberg et al., "Treatment of sickle cell anemia with hydroxyurea and erythropoietin" *N. Engl. J. Med.* (1990) 323:366–372.

Lazzarino et al., "Treatment of terminal–phase chronic myelogenous leukemia with intermediate–dose cytarabine and hydroxyurea" *Hematol. Oncol.* (1991) 9:299–305.

Moore et al., "Analysis of gene transfer in bone marrow stem cells" *Gene Targeting: A Practical Approach (Practical Approach Series, 125)* Joyner, A.L., Ed., IRL Press (1993) Chapter 3, pp. 63–77 and 100–106.

Yorifuji et al. "The effect of cell synchronization on the efficiency of stable gene transfer by electroporation" (1989) *FEBS Letters* 245:201–203.

MPB HSCs
CTX + G-CSF

POST MOBILIZATION
HEMATOPOIESIS
SPLEEN HSCs
(CTX + G-CSF)

MM, ARKANSAS
(CTX + GM-CSF)

METHODS FOR GENE TRANSFER

TECHNICAL FIELD

This invention relates to the field of hematopoietic stem cell gene therapy and bone marrow transplantation.

BACKGROUND

Most mature blood cells are short lived and must be replaced continuously throughout adult life. Lifelong production of mature blood cells depends on the activity of a small pool of multipotential hematopoietic stem cells (HSC) located mainly in the bone marrow. These stem cells are capable of self-renewal and the generation of progenitor cells committed irreversibly to one of three main progenitor cell types: erythroid, myeloid and lymphoid. Erythroid progenitor cells give rise to erythrocytes. The myeloid lineage produces neutrophils and monocytes as well as platelets, mast cells, eosinophils and basophils. The lymphoid lineage gives rise to B and T lymphocytes and NK cells.

The ability of stem cells to undergo substantial self-renewal as well as the ability to proliferate and differentiate into all of the hematopoietic lineages makes stem cells the target of choice for a number of gene therapy applications. Successful gene transfer into stem cells should provide long-term repopulation of an individual with the modified cells and their progeny, which will express the desired gene product. There are many diseases that affect hematopoietic cells for which gene therapy and/or bone marrow transplantation could be useful to alleviate or cure the disease. Such diseases include severe combined immunodeficiency (SCID), chronic myelogenous leukemia (CML), β-thalassemia, sickle cell anemia and the like. Since blood cells have a finite life cycle, gene transfer into more mature hematopoietic cells, such as T cells, at best, provides only transient therapeutic benefit. For example, a SCID patient was treated by introducing a normal ADA gene into her lymphocytes ex vivo and reinjecting the transduced lymphocytes back into the patient (Biotechnology News (1993) 13:14). For effective therapy, ADA-carrying lymphocytes had to be reinjected into the patient every six months. Introducing the ADA gene into HSCs could obviate repeated treatments since the ADA-carrying stem cells could repopulate the bone marrow and completely cure the disease. Thus, gene therapy efforts are focused on hematopoietic stem cells because the transduction and transplantation of these cells would provide a means of ensuring a continuous supply of genetically modified hematopoietic cells during the lifetime of the patient. Hematopoietic stem cells are also ultimately responsible for restoring blood cell numbers if the hematopoietic system is depleted in some way.

DNA and retroviruses as well as other types of nucleic acid delivery vehicles, have been used to transfer genes in gene therapy. The use of retroviral vectors to mediate gene therapy is preferred over other vectors for nucleic acid transduction because of their high transduction efficiency. Other advantages include the reduced possibility of gene rearrangement and the single or low copy number transfer of the gene of interest. However, transducing HSCs presents a challenge because the stem cells are found in low numbers in bone marrow and are primarily quiescent. Retroviral integration and stable transduction of HSCs and their progeny require that the cells be in active cell cycle. A large fraction of the stem cells are in G0 phase of the cell cycle, that is, they are not actively cycling (Gordon et al. (1994) Leukemia 8:1068–1073). Efforts to optimize conditions for HSC transduction have focused on increasing the proportion of stem cells in cycle.

Cytokines have been used to induce cycling in cultured stem cells. For example, Reddy et al. (1995) Exp. Hematol. 23:813, reported that purified bone marrow stem/progenitor cells synchronously progressed from G0/G1 to S phase in vitro in response to a cytokine cocktail consisting of IL-3, IL-1α, bFGF, GM-CSF, G-CSF CSF-1 and steel factor. Peters et al. (1995) Exp. Hematol. 23:461, described a cytokine cocktail of IL-3, IL-6, IL-11 and SCF used to expand murine hematopoietic progenitor cells in 48 hour in vitro culture of bone marrow. However, treatment with these and other cocktails of cytokines trigger differentiation of the cell; therefore, pluripotency is lost. IL-7 was found to inhibit proliferation in vitro of leukemic cells isolated from some acute lymphoblastic leukemia (ALL) by arresting the cells at late G1 but the growth inhibition was accompanied by maturation of the cells (Skonsberg et al. (1991) Blood 77:2445–2450). In another approach, mouse bone marrow cells were arrested in G1/G0 phase by culturing the cells in isoleucine-free medium (Reddy et al. (1995) Exp. Hematol. 23:813).

A preincubation of harvested bone marrow cells in cytokines is routinely used to enhance the retroviral transduction efficiency by stimulating the cells to enter active cell cycle. One such protocol for enhancing retroviral integration was described by Kittler et al. (1994) Blood 84:344A. The procedure involved prestimulating isolated murine bone marrow cells in medium containing a cocktail of cytokines for 48 hours, then co-culturing for an additional 48 hours in the same medium and cytokines with the retroviral producer cell line. The cells were then injected into host mice. This regimen however, produced low levels of engraftment in bone marrow and failed to achieve retroviral transduced cells in the bone marrow or in peripheral blood. Another procedure involved the pretreatment of mice with 5-fluorouracil (5-FU) and the addition of growth factors (IL-3, IL-6 or both) during or before the cocultivation of stem cells with virus producing cells prior to bone marrow transplantation (Bodine et al. (1991) Exp. Hematol. 19:206). However, 5-FU is a toxic drug.

The reported methods of triggering stem cells to enter the cell cycle either by the use of cytokines or other reagents have mostly been performed in vitro or ex vivo. Yet one study describes the use of a dekapeptide (pEEDCK)$_2$ injected into mice to trigger quiescent CFU-s (colony forming units) into the cell cycle, thus inducing a stem cell population expansion. (Paukovits et al. (1995) Cancer Research Therapy & Control, 4:203–209).

Thus, for long term success of hematopoietic stem cell gene therapy, there remains a need for efficient vector integration and maintenance of stem cell pluripotency. It is desirable to achieve a method of enriching or inducing for HSCs that are in active cycle without loss of pluripotency. In addition, the method should be applicable in vivo with minimal toxicity to the individual receiving treatment. The present invention satisfies these needs and provides related advantages as well.

DESCRIPTION OF THE INVENTION

The present invention provides a method of enhancing gene transfer in hematopoietic stem cells (HSCs), by contacting the HSCs with an effective amount of hydroxyurea prior to gene transfer. An effective amount is the amount of HU effective to induce HSCs in G0 into active cell cycle. This method is suitable for gene transfer performed in vitro, in vivo or ex vivo.

Another embodiment of the invention is a method of treating a subject suffering from a disease amenable to gene therapy by administering hydroxyurea to the subject in an amount effective to induce HSCs in G0 into active cell cycle or accumulating in late G1 early S all cells that the treatment interval went into cycle, followed by administering the individual with a therapeutic gene suitable to alleviate the disease.

Finally, the invention provides a method of enhancing the efficacy of bone marrow transplantation, wherein hydroxyurea is administered to a bone marrow donor prior to harvesting the bone marrow. The bone marrow donor receives an amount of hydroxyurea effective to increase the number of HSCs available for transplantation.

BRIEF DESCRIPTION OF THE DRAWINGS

FIG. 5A shows long term reconstitution of multi-lineage reconstitution in representative mouse 8457E-3. FIG. 5B shows multi-lineage reconstitution with transient myelopoiesis in representative mouse 8459B-2.

MODE(S) FOR CARRYING OUT THE INVENTION

Figure 1A:
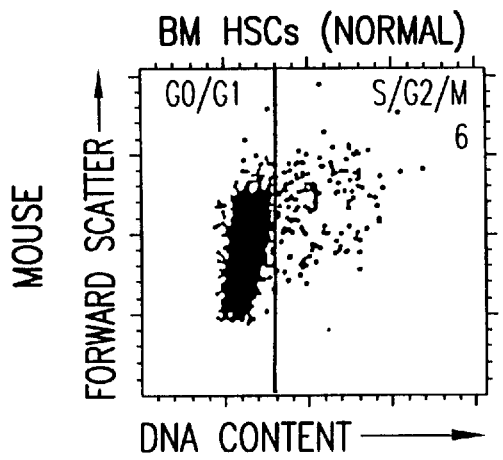
FIG. 1, panels A through G, shows the percentage of HSCs in active cell cycle in the bone marrow and the percentage in the periphery following mobilization with cytokine and/or chemotherapeutic agents. Mouse HSCs are selected on the basis of staining for c-kit$^+$Thy-1.1$^{lo}$Lin$^{-/lo}$Sca-1$^+$ (KTLS). Human HSCs are selected for CD34$^+$Thy-1$^+$Lin$^-$. BM=bone marrow; MPB=mobilized peripheral bone marrow; CTXL=cyclophosphamide.
Figure 1B:
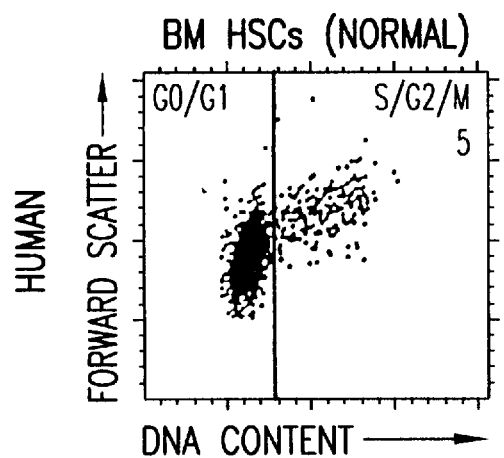
Figure 1C:
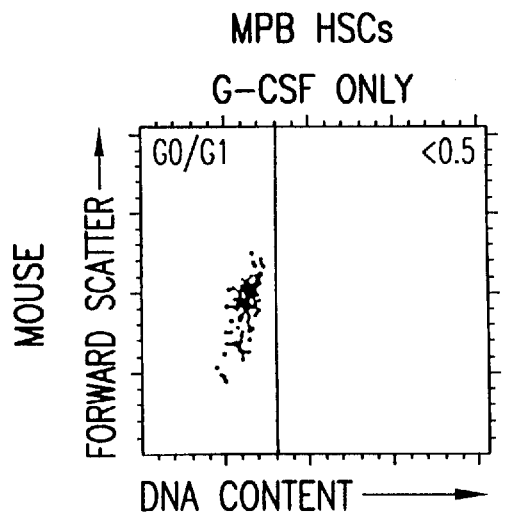
Figure 1D:
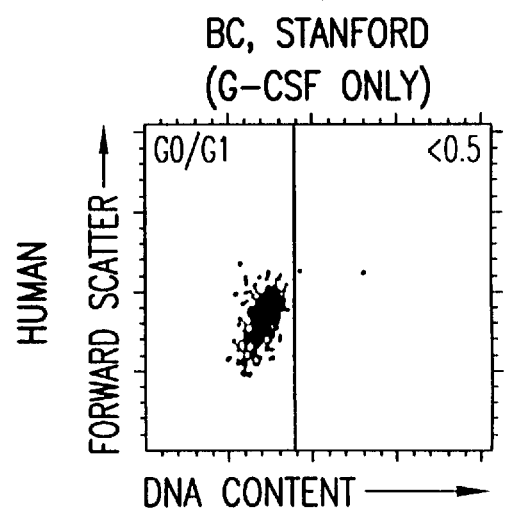
Figure 1E:
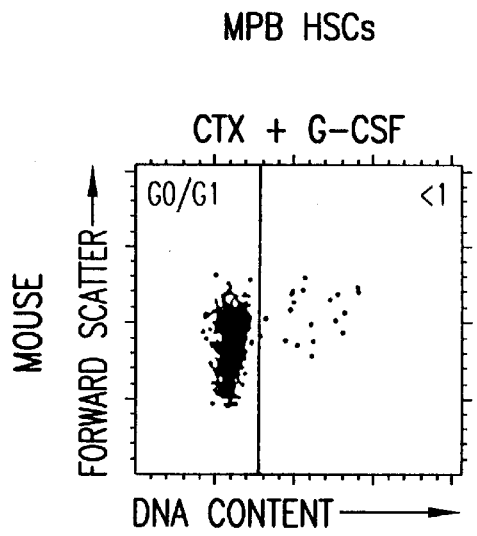
Figure 1G:
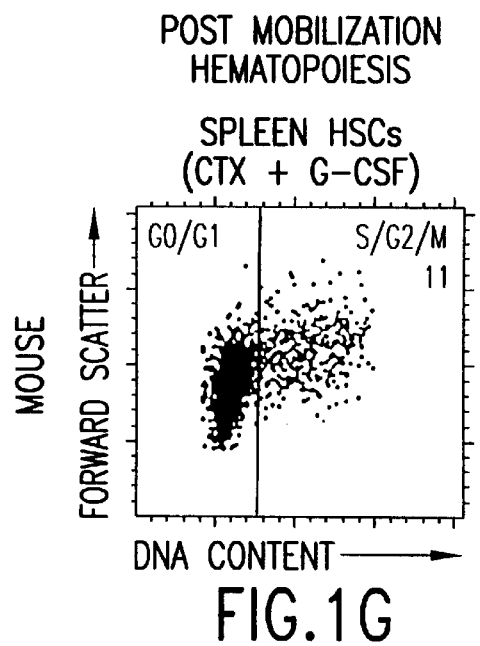
Figure 1F:
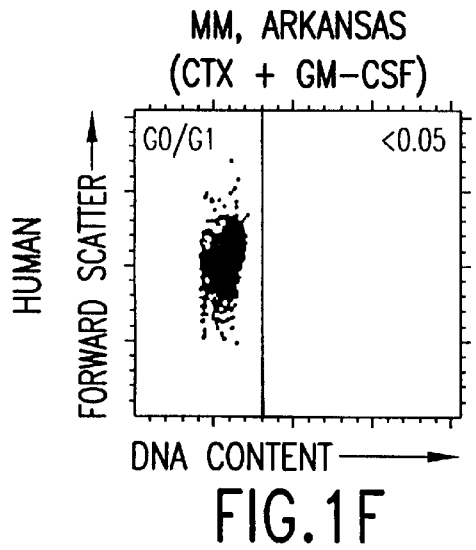
Figure 2A:
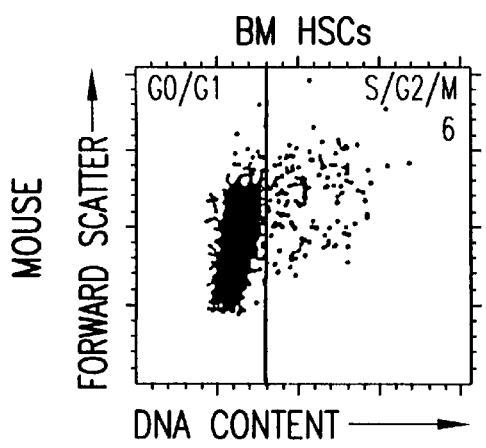
FIG. 2, panels A through F, shows that treatment with hydroxyurea increases the percentage of HSCs in BM and in addition, induces and/or accumulates mobilized peripheral HSC into the mitotic cycle.
Figure 2B:
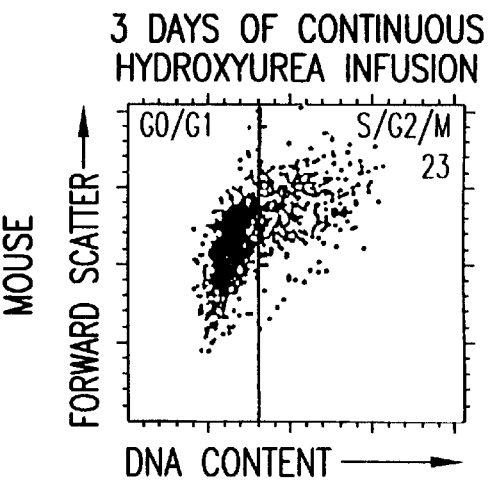
Figure 2E:
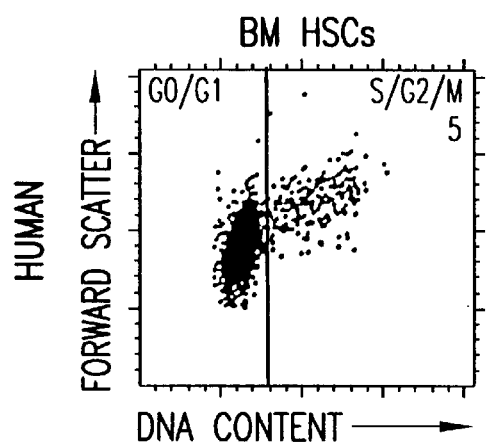
Figure 2C:
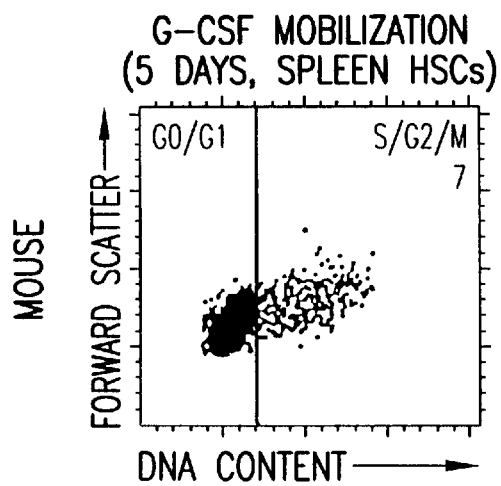
Figure 2D:
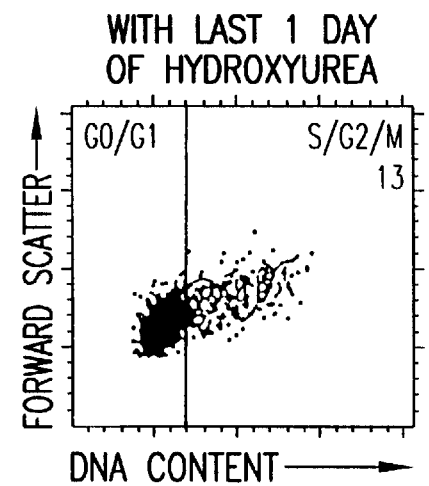
Figure 2F:
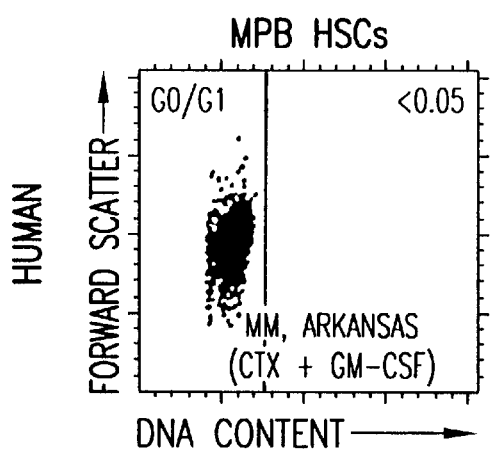
Figure 3B:
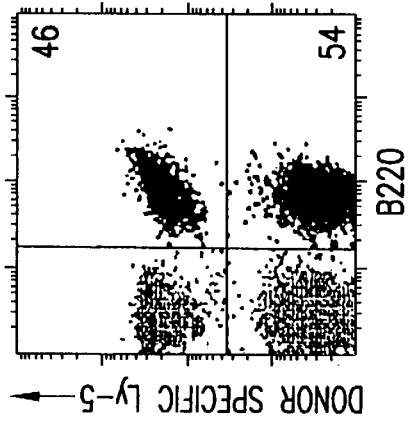
FIG. 3 (six panels, A through F) shows multilineage reconstitution from transplanting purified c-kit$^+$Thy-1.1$^{lo}$Lin$^{-/lo}$Sca-1$^+$ (KTLS) cells isolated from mice treated with 100 mg/kg/day of HU for 3 days prior to isolation of KTLS stem cells. The percentages of Ly-5-marked Mac-1$^+$ & Gr-1$^+$, B220$^+$ or CD3$^+$ cells originating from transplanted KTLS cells in a representative mouse are indicated in each panel. Top row shows mouse injected with 10 KTLS cells and analyzed at week 24. The bottom row shows a representative mouse injected with 50 S/G2/M Rh123$^{mid}$ KTLS cells and analyzed at week 16.
Figure 3C:
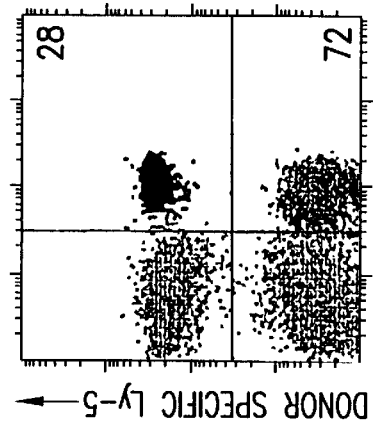
Figure 3A:
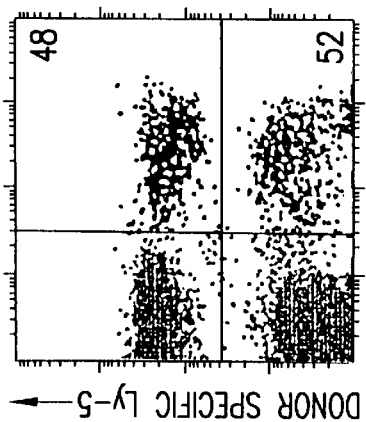
Figure 3E:
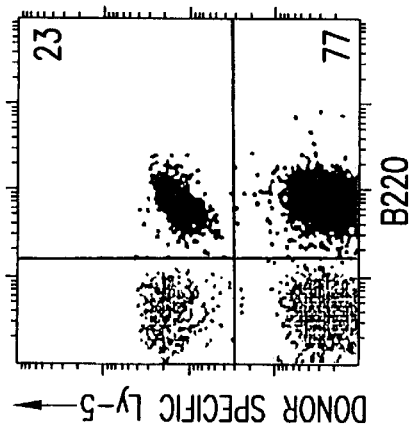
Figure 3F:
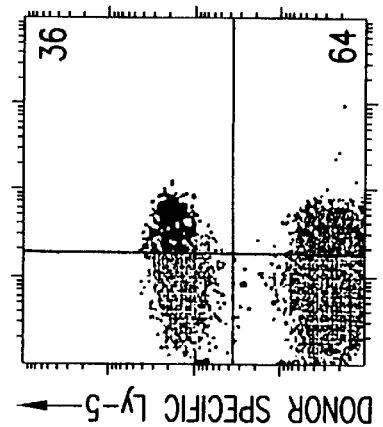
Figure 3D:
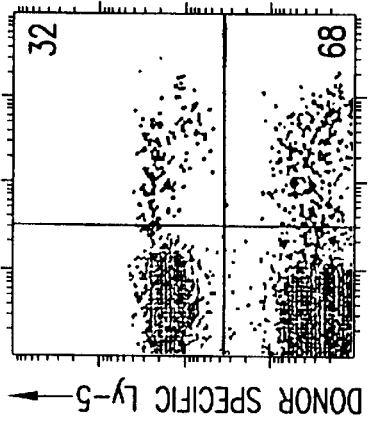

The present invention provides a method of enhancing nucleic acid integration during gene transfer and gene therapy by increasing the proportion of HSCs in active cell cycle prior to transduction. The method involves contacting the HSCs with the drug hydroxyurea in preparation for gene therapy. Contacting is effected in vitro, ex vivo or in vivo. After HU treatment, the HSCs are contacted with a therapeutic gene. The present invention provides that the contacting be effected any of in vitro, ex vivo or in vivo and under suitable conditions whereby the nucleic acid or gene is integrated into HSCs. In embodiments wherein the HU treatment or HU treatment plus gene transfer occurs in vitro or ex vivo, the manipulated cells can be introduced into a recipient. For the purposes of this invention, HSCs are allogeneic or autologous to the recipient.

In vivo, the present invention provides a method of enhancing gene transfer in hematopoietic stem cells (HSCs) by accumulation of HSCs that are in active phases of the cell cycle, in the G1/S/G2/M phases. This is achieved by administering to a subject the drug, hydroxyurea, to induce HSCs in G0 into active cell cycle in vivo prior to and in preparation for, gene transfer.

The methods of this invention are intended to encompass any method of gene transfer into hematopoietic stem cells, including but not limited to viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. The methods are particularly suited for the integration of a nucleic acid contained in a vector or construct lacking a nuclear localizing element or sequence such that the nucleic acid remains in the cytoplasm. In these instances, the nucleic acid or therapeutic gene is able to enter the nucleus during M (mitosis) phase when the nuclear membrane breaks down and the nucleic acid or therapeutic gene gains access to the host cell chromosome. In one embodiment, nucleic acid vectors and constructs having a nuclear localizing element or sequence are specifically excluded.

The present methods are particularly suited for retroviral mediated gene transfer. In retroviral transduction, the transferred sequences are stably integrated into the chromosomal DNA of the target cell. Conditions that favor stable proviral integration include actively cycling cells. HSCs are present in very low numbers, constituting only about 0.01% of all cells in the bone marrow; a large proportion of them are not actively cycling. One embodiment of the invention is a method for enhancing retroviral mediated gene transfer that involves synchronously switching G0 HSCs into the active cell cycle (G1/S/G2/M phases) by in vivo treatment with hydroxyurea. This treatment serves to accumulate cells in an "early" phase of the cell cycle before mitosis. This accumulation of stem cells in cycle serves many applications; most importantly, the increase in frequencies of HSCs at the active phases of the cell cycle when they are most susceptible to retroviral infection and integration of genes from retroviral constructs.

The terminology for the various stages of the cell cycle are as commonly used and understood in the art. G0 refers to the resting or nongrowing state in the cell cycle; G0 cells are considered noncycling. Cells can be induced to leave the G0 phase and enter into active cycle, i.e. G1, S, G2 and M phases. In culture, this has be achieved, for instance, by introducing growth factors into the culture medium which also induces the cells to differentiate thereby losing their pluripotent characteristic.

Hydroxyurea is a specific and potent inhibitor of DNA synthesis in mammalian cells (Timon (1975) Mut. Res.

32:115). It exerts its effects primarily by inhibiting ribonucleotide reductase thereby decreasing de novo synthesis of essential DNA precursors which leads to accumulation of cells in early S phase of the cell cycle (Eriksson et al. (1987) Exp. Cell. Res. 168:79–88). Administration of HU causes a reversible G1/S block in the cell cycle (Morse et al. (1969) Proc. Soc. Exp. Biol. Med. 130:986; Bhuyan et al. (1973) Cancer Res. 33:888). HU is preapproved for clinical administration; it is currently used as an anticancer drug, for example, in the treatment of chronic myelogenous leukemia (CML). Adult CML patients with advanced neoplasms have been treated with an oral dose of 50 mg/kg/day for an average duration of 11 days (Kennedy (1992) Seminars in Oncology, 19 :21–26). In the method of this invention, patients can be treated with HU for a much shorter duration, generally about 3 days but treatment can continue for any amount of time that is necessary and effective to achieve the desired result. The treatment does not pose any problems of toxicity. In fact, a major advantage of using hydroxyurea in the present method of treating humans is its low or negligible toxicity.

Since in vivo treatment with HU also enriches for HSCs in the bone marrow, the invention also encompasses a method of increasing hematopoietic stem cell yields for bone marrow transplantation by administering to the bone marrow donor an effective amount of HU prior to stem cell harvest.

The ability to accumulate cells in G1/S phase and to increase total HSC numbers upon in vivo treatment with HU also serve use to identify, isolate and study cell cycle specific factors involved in the differentiation, proliferation and/or self-renewal of HSCs. A better understanding of HSC cycle control, growth and differentiation is important in treating hematopoietic diseases; such knowledge will, for example, facilitate the optimization of timing and conditions for administering anti-proliferative drugs in cancer patients or provide new cell cycle specific proteins as targets for drug therapy in various HSC disease conditions. Cells treated with HU can be used, for example, in assays to screen for drugs that inhibit proliferation or reverse cell cycle arrest at G1/S. Therefore, another aspect of the invention is a method of identifying such cell specific factors by contacting HSCs with HU in an amount effective to induce HSC proliferation and analyzing the HU treated cells for the presence of specific factors in arrested or proliferating cells. The HU treated cells can be analyzed for changes not present in the non-HU treated control cells, changes that may take the form of difference in the levels of existng proteins, synthesis of new proteins, modifications to existing proteins that may activate or suppress their biological activity, association of proteins into functional complexes.

In a separate aspect, cells can be treated with HU and subsequently with a test agent to screen for the ability of the test agent to block or reverse the effects of HU. In this case, the control cells will be treated with HU but in the absence of the test agent or with the test agent in the absence of HU.

For example, a suitable sample of HSCs is removed from a donor, either before or after HU treatment. For HU treatment in vitro, CD34$^+$Thy-1$^+$Lin$^-$ (human) or murine kit$^+$Thy-1.1$^{lo}$Lin$^{-/lo}$Sca-1$^+$ (KTLS) stem cell populations are selected in vitro and contacted in vitro with an effective amount of HU to induce HSCs into active cell cycle. The HU treated cells are contacted with an agent to be tested for its effect on cycling HSCs (test agent). Contact with the test agent can be performed at various time intervals depending on the agent being tested and its intended purpose, i.e. prior to, concomitant with or subsequent to HU treatment.

The cells are then cultured under conditions that support proliferation, self-renewal or differentiation. The cells are then assayed to determine any biological effect of the test agent on the cell cycle status using the assays identified and exemplified herein.

I. Hydroxyurea Treatment and Gene Transfer

The present methods for stable transduction of HSCs and their progeny provides improved methods for humans although these methods also are practiced in any suitable subject, i.e., mammals such as mice, dogs, cats, horses, monkeys, etc. Mammals treated by the methods of this invention provide useful animal models for the study of gene transfer and for gene therapies. In vitro applications of the methods provide assay systems for the study and pre-clinical application of gene therapy.

The present methods also are preferably perfomed with HU. However, any agent that induces the cell into the active cycle from the G0 phase without toxicity is suitably substituted in the methods described herein.

Hematopoietic cells encompass HSCs, erythrocytes, neutrophils, monocytes, platelets, mast cells, eosinophils and basophils, B and T lymphocytes and NK cells as well as the respective lineage progenitor cells. As used herein, a hematopoietic stem cell (HSC) refers to a primitive or pluripotential hematopoietic stem cell that is capable of giving rise to progeny in all defined hematolymphoid lineages: limiting numbers of stem cells must be capable of fully reconstituting lethally irradiated mice, leading to their long-term survival. In humans, the CD34$^+$Thy-1$^+$Lin$^-$ hematopoietic stem cells are the equivalent of the murine kit$^+$Thy-1.1$^{lo}$Lin$^{-/lo}$Sca-1$^+$ (KTLS) hematopoietic stem cells and are a virtually pure population of multilineage hematopoietic stem cells.

Initial studies had suggested that CD34$^+$ cells were enriched for pluripotent hematopoietic stem cells (U.S. Pat. No. 5,035,994). U.S. Pat. No. 5,061,620 to Tsukamoto et al. stated that B cell and myeloid cell progenitors make up 80–90% of the CD34$^+$ cell population. Terstappen et al. (1992) Blood 79:666–677, has suggested that CD34 antigenic density decreases with maturation of hematopoeitic cells and increased CD38 cell population. Further studies have shown that CD34 expression is not limited to pluripotent stem cells. When CD34 expression is combined with selection for Thy-1, a composition comprising fewer than 5% of lineage committed cells can be isolated (U.S. Pat. No. 5,061,620, columns 4 through 15).

Lin$^-$ refers to cells that are lineage negative, i.e., cells lacking markers such as those associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils. Methods of negative selection are known in the art. The absence or low expression of such lineage specific markers is identified by the lack of binding of antibodies specific to the cell specific markers, useful in so-called "negative selection". Preferably the lineage specific markers include, but are not limited to, at least one of CD2, CD14, CD15, CD16, CD19, CD20, CD38, HLA-DR and CD71; more preferably, at least CD14 and CD15. As used herein, Lin$^-$ refers to a cell population selected based on the lack of expression of at least one lineage specific marker. Antibodies specific to lineage specific markers are commercially available from various vendors, eg. Becton Dickinson, Caltag, AMAC and the ATCC.

Methods of determining the presence or absence of a cell surface marker are well known in the art. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992–1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionuclides, including, but not limited to, $^{14}$C, $^{3}$H and $^{35}$S.

Ex vivo and in vitro cell populations include, but are not limited to, cell populations obtained from bone marrow, both adult and fetal, mobilized peripheral blood (MPB) and umbilical cord blood. The use of umbilical cord blood is discussed, for instance, in Issaragrishi et al. (1995) N. Engl. J. Med. 332:367–369. Initially, bone marrow cells can be obtained from a source of bone marrow, including but not limited to, ileum (e.g., from the hip bone via the iliac crest), tibia, femora, vertebrate, or other bone cavities. Other sources of stem cells include, but are not limited to, embryonic yolk sac, fetal liver, and fetal spleen. The methods can include further enrichment or purification procedures or steps for stem cell isolation by positive selection for other stem cell specific markers.

When the invention is practiced in vitro or ex vivo, it can be desirable to enrich for the CD34$^+$Thy-1$^+$Lin$^-$ cell composition prior to gene transfer and/or HU treatment. Preferably, the cell population is initially subjected to negative selection techniques to remove those cells that express lineage specific markers and retain those cells which are lineage negative ("Lin$^-$").

Various techniques can be employed to separate the cells by initially removing cells of dedicated lineage. Monoclonal antibodies are particularly useful for identifying markers associated with particular cell lineages and/or stages of differentiation. The antibodies can be attached to a solid support to allow for crude separation. The separation techniques employed should maximize the retention of viability of the fraction to be collected. Various techniques of different efficacy can be employed to obtain "relatively crude" separations. Such separations are up to 10%, usually not more than about 5%, preferably not more than about 1%, of the total cells present not having the marker can remain with the cell population to be retained. The particular technique employed will depend upon efficiency of separation, associated cytotoxicity, ease and speed of performance, and necessity for sophisticated equipment and/or technical skill.

Procedures for separation can include, but are not limited to, physical separation, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of physical separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

Preferred techniques that provide accurate separation include, but are not limited to, flow cytometry, which can have varying degrees of sophistication, e.g., a plurality of color channels, low angle and obtuse light scattering detecting channels, impedance channels, etc. Cells also can be selected by flow cytometry based on light scatter characteristics, where stem cells are selected based on low side scatter and low to medium forward scatter profiles. Cytospin preparations show the enriched stem cells to have a size between mature lymphoid cells and mature granulocytes.

As an illustration, in a first separation, typically starting with about $1\times10^{8-9}$, preferably at about $5\times10^{8-9}$ cells are labeled with a first fluorochrome, while the antibodies for the various dedicated lineages, are conjugated to a fluorochrome with different and distinguishable spectral characteristics from the first fluorochrome. While each of the lineages are separated in more than one "separation" step, desirably the lineages are separated at the same time as one is positively selecting for the stem cell markers CD34$^+$ and Thy-1$^+$. The cells are selected and isolated from dead cells, by employing dyes associated with dead cells (including but not limited to, propidium iodide (PI)). Preferably, the cells are collected in a medium comprising 2% FCS. These techniques are well known and described in various publications, for example, U.S. Pat. No. 5,061,620; U.S. Pat. No. 5,409,813; International Publication No. WO95/05843; Yau, et al. (1990) Exp. Hematol. 18:219–222; and Takaue (1986) Am. J. Hematol. (1986) 23:247–262).

For in vitro and ex vivo applications of the methods, cells are collected from an isolate of bone marrow. As an illustration, an appropriate solution is used to flush the bone, the solution including, but not limited to, salt solution, conveniently supplemented with fetal calf serum (FCS) or other naturally occurring factors, in conjunction with an acceptable buffer at low concentration, generally from about 5–25 mM. Convenient buffers include, but are not limited to, HEPES, phosphate buffers and lactate buffers. Otherwise bone marrow is aspirated from the bone in accordance with conventional techniques.

For cell sorting, the following is provided as an exemplary protocol. Fresh MPB (mobilized peripheral blood) samples are elutriated with a JE5.0 Beckman counterflow elutriator equipped with a Sanderson chamber (Beckman, Palo Alto, Calif.). Cells are resuspended in elutriation medium (Biowhittaker, Walkersville, Md.) at pH 7.2, supplemented with 0.5% human serum albumin (HSA). The rotor speed is set at 2000 RPM, the cells are introduced, and the first fraction collected at a flow rate of 9.6 ml/min. Fractions 2 and 3 are collected at the respective flow rates of 14 and 16 ml/min. The larger cells remaining in the chamber are collected after stopping the rotor. Cells are resuspended in RPMI supplemented with 5% HSA, 10 μg/ml DNAse I and penicillin/streptomycin at 50 U/ml and 50 μg/ml, respectively. Fractions 2 and 3 are pooled and incubated with 1 mg/ml heat-inactivated human gamma-globulin to block non-specific Fc binding. Granulocytes are further depleted by incubation with CD15 conjugated to magnetic beads (Dynal M450, Oslo, Norway) followed by magnetic selection.

Anti-CD34 antibody, e.g., Tuk 3 (IgG 3), or an IgG3 isotype matched control are added to cells in staining buffer (HBSS, 2% FCS, 10 mM HEPES) for 20 minutes on ice, together with anti-Thy-1 antibody, e.g., GM201, at 5 µg/ml. Cells are washed with a FCS underlay, and then incubated with Texas Red conjugated goat anti-mouse IgG3 antibody and phycoerythrin-conjugated goat anti-mouse IgG1 antibody for 20 minutes on ice. Blocking IgG1 is then added for 10 minutes. After blocking, the FITC-conjugated lineage antibody panel is added, and incubated for another 20 minutes on ice. After a final washing, cells are resuspended in staining buffer containing propidium iodide (PI).

Cells are sorted in the FACSTAR Plus cell sorter equipped with dual argon ion lasers, the primary laser emitting at 488 nm and a dye laser (Rhodamine 6G) emitting at 600 nm (Coherent Innova 90, Santa Cruz, Calif.). Residual erythrocytes, debris and dead cells are excluded by light scatter gating plus an FL3 (PI) low gate. Following isolation of a cell population by FACS, the sample is diluted 1:1 in HBSS, pelleted, and resuspended in HBSS for hemocytometer counting.

$CD34^+$ cells are positively selected from adult bone marrow (ABM) using a biotinylated anti-CD34 antibody (K6.1) and a biotin competition release according to the method described in PCT Publication No. WO94/02016.

Methods for mobilizing stem cells into the peripheral blood are known in the art and generally involve treatment with chemotherapeutic drugs, cytokines (e.g. GM-CSF, G-CSF or IL3), or combinations thereof. Typically, apheresis for total white cells begins when the total white cell count reaches 500–2000 cells/µl and the platelet count reaches 50,000/µl.

After HU treatment, the cells are transduced with a therapeutic gene. Preferably, the transduction is via a vector such as a retroviral vector. When transduction is ex vivo, the transduced cells are subsequently administered to the recipient. Thus, the invention encompasses treatment of diseases amendable to gene transfer into HSCs, by administering the gene ex vivo or in vivo by the methods disclosed herein. For example, diseases including, but not limited to, a-thalassemia, sickle cell anemia, adenosine deaminase deficiency, recombinase deficiency, recombinase regulatory gene deficiency, etc. can be corrected by introduction of a therapeutic gene. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Diseases other than those associated with hematopoietic cells can also be treated by genetic modification, where the disease is related to the lack of a particular secreted product including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Hydroxyurea is administered to an individual undergoing HSC gene therapy. The individual receiving HU treatment need not be the patient undergoing gene therapy but also can be a healthy bone marrow donor for a gene therapy patient who is suffering from a disease alleviated by gene therapy, e.g., a patient having a HSC deficiency or depletion or otherwise unable to receive HU treatment directly. After HU treatment and successful gene transfer in the bone marrow donor, the transduced HSCs are isolated from the donor and transplanted into the patient in need of gene therapy. Alternatively, the HSCs are removed and contacted with HU and transduced ex vivo. Since HU treatment enriches for pluripotent stem cells, bone marrow donors receiving HU prior to stem cell harvest and transplantation into the recipient provide enriched populations of HSCs for transplantation. This invention encompasses this therapy as well.

Hydroxyurea (HU, $CH_4N_2O_2$) is available commercially as Hydrea, Bristol-Myers Squibb, (Evansville, Ind.). HU is a crystalline powder freely soluble in water and slightly soluble in alcohol. For the purposes of this invention HU is included to encompass all pharmaceutically active derivatives (e.g., N-substituted and O-substituted analogs) of the compound including, but not limited to, prodrugs and the like. As used herein, the term "hydroxyurea" ("HU") is intended to include all pharmaceutically active analogs, derivatives and prodrugs.

Inhibition of DNA synthesis by HU is dose dependent. The half life of the drug is about 5 hours. HU is used clinically in the treatment of various cancers and sickle cell anemia. Adult CML patients have been treated with an oral dose of 50 mg/kg/d for an average duration of 11 days (Kennedy (1992) Seminars in Oncology, 19:21–26). Sickle cell anemia was effectively treated by administration of initial dose of 15 mg/kg body weight per day, increased by 5 mg/kg body weight per day every 12 weeks for up to two years of therapy. Dosing was achieved by an oral tablet formulation (Charche et al. (1995) N. Eng. J. Med. 332:1317–1322). Intravenous infusion of HU was shown to be safe in doses up to 48 grams in 48 hours, 3 times per week (Veale et al. (1988) Chemother. Pharmacol. 21:53–56).

In the present method, HU is administered to the subject in an amount effective to induce HSCs in G0 to enter G1/S/G2/M phases of the cell cycle. This amount is readily determined by procedures familiar to one of ordinary skill in the art. For example, a titration of HU dosages is administered to human volunteers and the effect of each dose on the number of HSCs at G1/S/G2/M phases of the cycle is determined. As suitable controls, the number of cycling HSCs before HU treatment and/or with placebo treatment also is determined. The dosage that produces on average the highest number of actively cycling HSCs without adverse effects or toxicity, is the optimum dosage and will usually be the dosage used in treatment. It will be understood that the optimum dosage may vary with the subject being treated (age, general health, gender etc.) and the route of administration. These variables will be taken into account in determining effective and optimum dosages. The determination of effective dosage requires testing with different routes of drug administration. There are instances when a lower than optimum dosage of HU is used with particular patients due to various reasons, for example, incompatibility with other medication used concurrently. However, any dosage of HU effective to increase the number of HSCs in G1/S/G2/M phases by at least 1.5 fold, preferably 2 fold or greater, over that in the non-HU treated situation will increase the efficiency of gene transfer. Accordingly, for the purposes of this invention, the term "enhancing" means at least a 1.5 fold increase over that in the non-HU treated subject or control. The effective amount of HU will generally be in the range of 10–200 mg/kg body weight per day, and the drug will be administered continuously for a period of at least 2 days, generally for about 2 to 14 days. In a particular embodiment, HU is administered in an amount effective to produce at least a 10–20% increase of HSCs in S/G2/M phases of the cell cycle. Increasing the duration of HU treatment increases the total percentage of cycling HSCs. Toxicity requiring modification of drug dosage is defined as absolute neutrophil counts less than $2.5 \times 10^9$/L, platelet counts less than 100,000/mm$^3$ and a decrease in Hb concentration of 20% or more (Vichinksy and Lubin (1994) Blood 83(4):1124–1128).

Immediately before HU treatment, it is desirable to obtain a sample of bone marrow cells to provide a baseline for cell numbers and the cell cycle status of the subject's HSCs. The phase of the cell cycle that a particular HSC is in is determined using standard procedures known in the relevant art. The quantification of HSCs in S, G2 and M phases will be generally be used as an indicator of the effect of HU on the cell cycle since it can be difficult to distinguish G1 from G0 cells to specifically assay for G1 cells. HSCs in S/G2/M phases can be determined such as by Hoescht dye, $3^H$ UTP or propidium iodide (PI). A sample of bone marrow cells is obtained and stained for HSCs as described above and in the Experimental Examples. In humans, cells that stain for CD34$^+$Thy-1$^+$Lin$^-$ are isolated, stained with rhodamine followed by staining with Hoeschst dye and analyzed for rhodamine fluorescence intensity using flow cytometry, as described under Experimental Examples.

In the present methods, HU is administered in various ways such as orally, by intravenous injection or by continuous infusion by i.v. drip, intraperitoneally or subcutaneously. For convenience, HU is administered orally in various formulations, including but not limited to a controlled release formulation. HU is readily absorbed from the GI tract. Studies indicate that orally administered HU is degraded in the liver and is excreted as respiratory carbon dioxide and as urea or in intact form in urine.

HU is administered in a variety of unit dosage forms depending upon the method of administration. For example, unit dosage forms suitable for oral administration include powder, tablets, pills, capsules and dragees. Intravenous administration will comprise a solution of HU dissolved or suspended in a pharmaceutically acceptable carrier, preferably an aqueous carrier. Slow release formulations, or slow release delivery vehicles are desirable for continuous administration.

In preparation for gene therapy, the individual is pretreated with HU at a dosage range of about 10–200 mg/kg body weight (b.w.) per day, preferably at about 50 mg/kg and even more preferably, at about 100 mg/kg. The duration of treatment is about 2–14 consecutive days, preferably about 2–7 days, even more preferably 3 days. In one aspect, HU is administered orally in equal dosages a few times a day to a total of 50–150 mg/kg b.w. per day. For example, the individual can receive an oral dose of 50 mg/kg b.w. twice daily at about 12 hour intervals. Alternatively, the patient is injected with HU at regular intervals 2–3 times a day. HU can also be administered by continuous i.v. drip, using well known methods as described in Vichinksy and Lubin (1994) supra. In a preferred embodiment, the individual is treated with 100 mg of HU per kg b.w. per day, in oral form, for 2–7 consecutive days prior to gene transfer or HSC harvest. Transduction is performed either during or subsequent to HU therapy.

In one embodiment, HU is administered in a pharmaceutically acceptable carrier. As used herein, the term "pharmaceutical carrier" or "pharmaceutical diluent" denotes a solid or liquid which by itself is devoid of activity attributed to HU and is composed of a single substance or any number of substances such as solids, liquids or both. Some examples of the substances which can serve as pharmaceutical carriers for HU are gelatin capsules; sugars, such as lactose and sucrose; starches, such as corn starch and potato starch; cellulose derivatives, such as sodium carboxymethyl cellulose, ethyl cellulose, methyl cellulose, cellulose acetate phthalate; gelatin; talc; stearic acid; magnesium stearate; vegetable oils; such as peanut oil, cottonseed oil, sesame oil, olive oil, corn oil and oil of theobroma; propylene glycol; glycerin; sorbitol; polyethylene glycol; water, agar; alginic acid; isotomic saline; and phosphate buffer solutions, as well as other non-toxic compatible substances used in pharmaceutical formulations including coloring, flavoring and preservatives. Pharmaceutically acceptable carriers are described, e.g., in the Merck Index, Merck & Co., Rahway, N.J.

Following HU treatment, the HSCs of the treated individual are subjected to gene transfer using any suitable vectors but preferably by viral infection/transduction with a viral vector carrying a suitable therapeutic gene. Optionally, it is desirable to quantify total HSCs and cycling HSCs following HU treatment and before gene transfer. Quantification can be performed using procedures described above.

Vectors for Gene Transfer

As noted above, any method of gene transfer is encompassed by this invention. As used herein, "viral vector" is defined as a recombinantly produced virus or viral particle that comprises a polynucleotide to be delivered into a host cell, either in vivo, ex vivo or in vitro. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

Retroviral vectors useful in the methods of this invention are produced recombinantly by procedures already taught in the art. For example, WO 94/29438 describes the construction of retroviral packaging plasmids and packaging cell lines. As is apparent to the skilled artisan, the retroviral vectors useful in the methods of this invention are capable of infecting HSCs. The techniques used to construct vectors, and transfect and infect cells are widely practiced in the art. Examples of retroviral vectors are those derived from murine, avian or primate retroviruses. Retroviral vectors based on the Moloney (Mo) murine leukemia virus (MuLV) are the most commonly used because of the availability of retroviral variants that efficiently infect human cells. Other suitable vectors include those based on the Gibbon Ape Leukemia Virus (GALV) or HIV.

In producing retroviral vector constructs derived from the Moloney murine leukemia virus (MoMLV), in most cases, the viral gag, pol and env sequences are removed from the virus, creating room for insertion of foreign DNA sequences. Genes encoded by the foreign DNA are usually expressed under the control of the strong viral promoter in the LTR. Such a construct can be packed into viral particles efficiently if the gag, pol and env functions are provided in trans by a packaging cell line. Thus, when the vector construct is introduced into the packaging cell, the gag-pol and env proteins produced by the cell, assemble with the vector RNA to produce infectious virions that are secreted into the culture medium. The virus thus produced can infect and integrate into the DNA of the target cell, but does not produce infectious viral particles since it is lacking essential packaging sequences. Most of the packaging cell lines currently in use have been transfected with separate plasmids, each containing one of the necessary coding sequences, so that multiple recombination events are necessary before a replication competent virus can be produced. Alternatively, the packaging cell line harbors an integrated provirus. The provirus has been crippled so that, although it produces all the proteins required to assemble infectious viruses, its own RNA cannot be packaged into virus. Instead, RNA produced from the recombinant virus is packaged. The virus stock released from the packaging cells thus contains only recombinant virus.

The range of host cells that may be infected by a retrovirus or retroviral vector is determined by the viral envelope protein. The recombinant virus can be used to infect virtually any other cell type recognized by the env protein provided by the packaging cell, resulting in the integration of the viral genome in the transduced cell and the stable production of the foreign gene product. In general, murine ecotropic env of MoMLV allows infection of rodent cells, whereas amphotropic env allows infection of rodent, avian and some primate cells, including human cells. Amphotropic packaging cell lines for use with MoMLV systems are known in the art and commercially available and include, but are not limited to, PA 12 and PA317. Miller et al. (1985) Mol. Cell. Biol. 5:431–437; Miller et al. (1986) Mol. Cell. Biol. 6:2895–2902; and Danos et al. (1988) Proc. Natl. Acad. Sci. USA 85:6460–6464. Xenotropic vector systems exist which also allow infection of human cells.

The host range of retroviral vectors has been altered by substituting the env protein of the base virus with that of a second virus. The resulting, "pseudotyped", virus has the host range of the virus donating the envelope protein and expressed by the packaging cell line. Recently, the G-glycoprotein from vesicular stomatitis virus (VSV-G) has been substituted for the MoMLV env protein. Burns et al. (1993) Proc. Natl. Acad. Sci USA 90:8033–8037; and PCT patent application WO 92/14829. Since infection is not dependent on a specific receptor, VSV-G pseudotyped vectors have a broad host range.

Usually, the vectors will contain at least two heterologous genes or gene sequences: (i) the therapeutic gene to be transferred; and (ii) a marker gene that enables tracking of infected cells. As used herein, "therapeutic gene" can be an entire gene or only the functionally active fragment of the gene capable of compensating for the deficiency in the patient that arises from the defective endogenous gene. Therapeutic gene also encompasses antisense oligonucleotides or genes useful for antisense suppression and ribozymes for ribozyme-mediated therapy. Therapeutic genes that encode dominant inhibitory oligonucleotides and peptides as well as genes that encode regulatory proteins and oligonucleotides also are encompassed by this invention. Generally, gene therapy will involve the transfer of a single therapeutic gene although more than one gene may be necessary for the treatment of particular diseases. In one embodiment, the therapeutic gene is a normal, i.e. wild-type, copy of the defective gene or a functional homolog. In a separate embodiment, the therapeutic gene is a dominant inhibiting mutant of the wild-type. More than one gene can be administered per vector or alternatively, more than one gene can be delivered using several compatible vectors. Depending on the genetic defect, the therapeutic gene can include the regulatory and untranslated sequences. For gene therapy in human patients, the therapeutic gene will generally be of human origin although genes from other closely related species that exhibit high homology and biologically identical or equivalent function in humans may be used, if the gene product does not induce an adverse immune reaction in the recipient. For example, a primate insulin gene whose gene product is capable of converting glucose to glycogen in humans would be considered a functional equivalent of the human gene. The therapeutic gene suitable for use in treatment will vary with the disease. For example, a suitable therapeutic gene for treating sickle cell anemia is a normal copy of the β-globin gene. A suitable therapeutic gene for treating SCID is the normal ADA gene.

Nucleotide sequences for the therapeutic gene will generally be known in the art or can be obtained from various sequence databases such as GenBank. The therapeutic gene itself will generally be available or can be isolated and cloned using the polymeran chain reaction PCR (Perkin-Elmer) and other standard recombinant techniques. The skilled artisan will readily recognize that any therapeutic gene can be excised as a compatible restriction fragment and placed in a vector in such a manner as to allow proper expression of the therapeutic gene in hematopoietic cells.

A marker gene can be included in the vector for the purpose of monitoring successful transduction and for selection of cells into which the DNA has been integrated, as against cells which have not integrated the DNA construct. Various marker genes include, but are not limited to, antibiotic resistance markers, such as resistance to G418 or hygromycin. Less conveniently, negative selection may be used, including, but not limited to, where the marker is the HSV-tk gene, which will make the cells sensitive to agents such as acyclovir and gancyclovir. Alternatively, selections could be accomplished by employment of a stable cell surface marker to select for transgene expressing stem cells by FACS sorting. The NeoR (neomycin/G418 resistance) gene is commonly used but any convenient marker gene whose sequences are not already present in the recipient cell, can be used.

The viral vector can be modified to incorporate chimeric envelope proteins or nonviral membrane proteins into retroviral particles to improve particle stability and expand the host range or to permit cell type-specific targeting during infection. The production of retroviral vectors that have altered host range is taught, for example, in WO 92/14829 and WO 93/14188. Retroviral vectors that can target specific cell types in vivo are also taught, for example, in Kasahara et al. (1994) Science 266:1373–1376. Kasahara et al. describe the construction of a Moloney leukemia virus (MoMLV) having a chimeric envelope protein consisting of human erythropoietin (EPO) fused with the viral envelope protein. This hybrid virus shows tissue tropism for human red blood progenitor cells that bear the receptor for EPO, and is therefore useful in gene therapy of sickle cell anemia and thalassemia. Retroviral vectors capable of specifically targeting infection of HSCs are preferred for in vivo gene therapy.

The viral constructs can be prepared in a variety of conventional ways. Numerous vectors are now available which provide the desired features, such as long terminal repeats, marker genes, and restriction sites, which may be further modified by techniques known in the art. The constructs may encode a signal peptide sequence to ensure that genes encoding cell surface or secreted proteins are properly processed post-translationally and expressed on the cell surface if appropriate. Preferably, the foreign gene(s) is under the control of a cell specific promoter.

Expression of the transferred gene can be controlled in a variety of ways depending on the purpose of gene transfer and the desired effect. Thus, the introduced gene may be put under the control of a promoter that will cause the gene to be expressed constitutively, only under specific physiologic conditions, or in particular cell types.

The retroviral LTR (long terminal repeat) is active in most hematopoietic cells in vivo and will generally be relied upon for transcription of the inserted sequences and their constitutive expression (Ohashi et al. (1992) Proc. Natl. Acad. Sci. 89:11332; Correll et al. (1992) Blood 80:331). Other suitable promoters include the human cytomegalovirus (CMV) immediate early promoter and the U3 region promoter of the Moloney Murine Sarcoma Virus (MMSV), Rous Sarcoma Virus (RSV) or Spleen Focus Forming Virus (SFFV).

Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells.

Inducible promoters may be used for gene expression under certain physiologic conditions. For example, an electrophile response element may be used to induce expression of a chemoresistance gene in response to electrophilic molecules. The therapeutic benefit may be further increased by targeting the gene product to the appropriate cellular location, for example the nucleus, by attaching the appropriate localizing sequences.

The vector construct is introduced into a packaging cell line which will generate infectious virions. Packaging cell lines capable of generating high titers of replication-defective recombinant viruses are known in the art, see for example, WO 94/29438. Viral particles are harvested from the cell supernatant and purified for in vivo infection using methods known in the art such as by filtration of supernatants 48 hours post transfection. The viral titer is determined by infection of a constant number of appropriate cells (depending on the retrovirus) with titrations of viral supernatants. The transduction efficiency can be assayed 48 hours later by both FACS and Southern blotting.

After viral transduction, the presence of the viral vector in the transduced stem cells or their progeny can be verified such as by PCR. PCR can be performed to detect the marker gene or other virally transduced sequences. Generally, periodic blood samples are taken and PCR conveniently performed using eg. NeoR probes if the NeoR gene is used as marker. The presence of virally transduced sequences in bone marrow cells or mature hemotopoietic cells is evidence of successful reconstitution by the transduced HSCs. PCR techniques and reagents are well known in the art, See, generally, *PCR Protocols, A Guide to Methods and Applications*. Innis, Gelfand, Sninsky & White, eds. (Academic Press, Inc., San Diego, 1990) and commercially available (Perkin-Elmer).

In another embodiment of the method, gene transfer is performed ex vivo. HSCs are harvested from the bone marrow or peripheral blood of the donor prior to or subsequent to HU treatment and infected with the retroviral vector carrying a suitable therapeutic gene. HU can be added to the transducing medium prior to and in some aspects, during transduction in an amount and under suitable conditions to allow for efficient retroviral infection and integration into HSCs.

Application of HSC Gene Therapy

A number of human genetic diseases that result from a lesion in a single gene are prime candidates for gene therapy. As used herein, the term "gene therapy" or "gene transfer" is defined as the insertion of genes into cells for the purpose of medicinal therapy. There are many applications of gene therapy, particularly via stem cell genetic insertion, and thus are well known and have been extensively reviewed.

Gene therapy using HSCs is useful to treat a genetic abnormality in lymphoid and myeloid cells that results generally in the production of a defective protein or abnormal levels of expression of the gene. For a number of these diseases, the introduction of a normal copy or functional homolog of the defective gene and the production of even small amounts of the missing gene product would have a beneficial effect. At the same time, overexpression of the gene product would not be expected to have deleterious effects. The following provides a non-exhaustive list of diseases for which gene transfer into HSCs is potentially useful. These diseases generally include bone marrow disorders, erythroid cell defects, metabolic disorders and the like. Hematopoietic stem cell gene therapy is beneficial for the treatment of genetic disorders of blood cells such as $\alpha$ and $\beta$-thalassemia, sickle cell anemia and hemophilia A and B in which the globin gene or clotting factor gene is defective. Another good example is the treatment of severe combined immunodeficiency disease (SCIDS), also known as the bubble boy syndrome, in which patients lack the adenosine deaminase (ADA) enzyme which helps eliminate certain byproducts that are toxic to T and B lymphocytes and render the patients defenseless against infection. Such patients are ideal candidates to receive gene therapy by introducing the ADA gene into their HSCs instead of the patient's lymphocytes as done in the past. Other diseases include chronic granulomatosis where the neutrophils express a defective cytochrome b and Gaucher disease resulting from an abnormal glucocerebrosidase gene product in macrophages.

Strategies to treat various forms of cancer also include gene therapy. The retroviral vector can carry a gene that encodes, for eg., a toxin or an apoptosis inducer effective to specifically kill the cancerous cells. Specific killing of tumor cells can also be accomplished by introducing a suicide gene to cancerous hematopoietic cells under conditions that only the tumor cells express the suicide gene. The suicide gene product confers lethal sensitivity to the cells by converting a normally nontoxic drug to a toxic derivative. For example, the enzyme cytosine deaminase converts the nontoxic substance 5'-fluorocytosine to a toxic derivative, 5-fluorouracil (Mullen et al. (1992) Proc. natl. Acad. Sci. USA 89:33–37). Tumor-specific lymphocytes can be genetically modified for example, to locally deliver gene products with anti-tumor activity to sites of the tumor to circumvent the toxicity associated with the systemic delivery of these gene products. A gene therapy approach can also be applied to render bone marrow cells resistant to the toxic effects of chemotherapy.

Gene therapy can also be used to prevent or combat viral infections such as HIV and HTLV-1 infection. For example, HSCs can be genetically modified to render them resistant to infection by HIV. One approach is to inhibit viral gene expression specifically by using antisense RNA or by subverting existing viral regulatory pathways. Antisense RNAs complementary to retroviral RNAs have been shown to inhibit the replication of a number of retroviruses (To et al. (1986) Mol. Cell. Biol. 6:4758–4762; Hopper and Coffin (1988) In: Gluzman and Hughes (eds.), *Current Communications in Biology, Viral Vectors*. Cold Spring Harbor Laboratory, Cold Spring Harbor, N.Y. pp 139–145) including HIV (Rhodes and James (1991) AIDS 5:145–151) and HTLV-1 (von Reuden et al. (1991) J. Virol. 63:677–682).

Another area where gene therapy in HSCs may find use is in alleviating autoimmune disease. The therapeutic gene can encode, eg., a B or T cell signalling molecule capable of reconstituting the normal apoptotic signal that results in the death and elimination of autoreactive cells.

II. Bone Marrow Transplantation

The invention also provides a method of enhancing the efficacy of bone marrow transplantation by administering hydroxyurea to a bone marrow donor in an amount effective to increase HSC yields prior to transplantation. After HU treatment, bone marrow cells are then harvested and transplanted into recipients following conventional procedures well known in the art of bone marrow transplantation. Gene therapy can be administered prior to transplantation.

A surprising and unexpected finding seen with HU treatment is the increase, not only in the number of HSCs that are now in active cycle, but in the total number of HSCs (see Table 1). These cells remain pluripotent as evidenced by the reconstitution of all hematopoietic lineages in transplanted host animals as demonstrated in the experimental examples and shown in FIG. 3 below. This enrichment in HSCs can be exploited for bone marrow transplantation for treating a variety of conditions described below.

In accordance with the present method, a bone marrow donor is treated with HU prior to transplantation, in an amount effective to increase the number of HSCs. The objective is to achieve a greater number of cycling stem cells than that available in the absence of treatment with HU, without producing adverse side effects and toxicity. Preferably, the number of HSCs in the bone marrow donor is increased by at least 1.5 fold after hydroxyurea administration. Administration of HU to the bone marrow donor is essentially as described above for the method of enhancing gene transfer. The optimum dosage will be the dosage that provides the highest number of HSCs without attendant toxicity as defined above.

The amount of HU effective to increase the number of HSCs can be readily determined, such as by measuring the number of HSCs before and after treatment with varying dosages of HU in the range of 10–200 mg /kg body weight per day. HU can be administered for varying lengths of time, eg., from 1–7 days. To measure HSC number, a bone marrow sample is isolated before or after HU treatment and bone marrow cells stained for $CD34^+Thy-1^+Lin^-$ surface markers indicative of HSCs. These cell isolation and staining procedures are standard in the art and are described in more detail in the experimental examples below. The numbers of $CD34^+Thy-1^+Lin^-$ stained cells present per unit volume of bone marrow are compared to determine the amount of HU effective to increase HSC numbers. The optimum dosage will generally be in the range of 50 mg–150 mg /kg body weight per day and treatment will be for a period of about 2 to 4 consecutive days. Preferably, hydoxyurea is administered intravenous infusion or orally. Side affects can be monitored using parameters familiar to one of average skill in the art of pharmocology.

HSCs are harvested from the bone marrow of the HU-treated donor for subsequent reintroduction into the bone marrow transplant recipient.

Many cancer patients receive intensive chemo- and/or radiotherapy to eradicate their tumour cells. This consists of several courses of chemotherapeutics, belonging to different classes, or irradiation. These courses put a high strain on the patient's bone marrow cells: Cycling bone marrow progenitors can be damaged and the primitive hematopoietic progenitor cells and hematopoietic stem cells will experience a high differentiative stress with the ultimate risk of exhaustion of these cells. Protective measures are thus warranted in order to rescue the patient's bone marrow and/or to intensify the chemo- or radiotherapy.

Autologous transplantation of bone marrow or of purified hematopoietic stem cells plays an important role to rescue patients from intensive chemo-/radiotherapy in certain acute leukemias, Hodgkin's and non-Hodgkin's lymphomas, multiple myeloma and selected solid tumors.

The methods provided by the present invention overcome at least 3 deficiencies of conventional protocols for gene transfer in HSCs: administration of HU in vivo produces actively cycling HSCs critical for retroviral infection and nucleic acid integration without the concomitant differentiation seen with cytokine treatment or the human toxicity seen with other drugs, as well as increases the number of HSCs available for gene transfer or transplantation.

Generally, the nomenclature used hereafter and the laboratory procedures in cell culture and recombinant technology described below are those well known and commonly employed in the art. The techniques and procedures are generally performed according to conventional methods in the art and various general references which are provided throughout this document. The procedures therein are believed to be well known in the art and are provided for the convenience of the reader.

The following examples are intended to illustrate, not limit, the invention described herein.

EXPERIMENTAL EXAMPLES

The following example describes the in vivo treatment of mice with HU and the resultant increase in the percentage of HSCs in S/G2/M phases as well as an increase in the total number of HSCs. This example also demonstrates the ability of the HU treated HSCs to produce long term reconstitution of hemopoiesis.

Mouse Strains

The C57BL/6-Ly-5.2-Pep3b (Thy-1.2, Ly-5.2), C57BL/Ka-Thy-1.1 (Thy-1.1, Ly-5.2), C57BL/Ka-Ly-5.1 (Thy-1.2, Ly-5.1), and C57BL/6-Ly-5.1-Pep3b-Thy-1.1 (Thy-1.1, Ly-5.1) mouse strains (defined based on Morse III et al. (1987) Immunogenetics 25:71–78) used in the study, were bred and maintained in the mouse facility at SyStemix.

Hydroxyurea Treatment

To initiate continuous hydroxyurea treatment to mice, mice were injected intraperitoneally with hydroxyurea at 10–100 mg/kg of body weight (b.w.). These HU treated mice were then anesthetized with a mixture of ketamine hydrochloride (50 mg/kg) and zylazine hydrochloride (25 mg/kg) and implanted with 7- or 14-day osmotic minipumps (Alza, Palo Alto, Calif.) containing either hydroxyurea (10–100 mg/kg/day) or PBS with 1% human serum albumin (control). After 1, 3 and 5 days, mice were sacrified to obtain long bones (two femurs and two tibias per mouse) for stem cell isolation.

Purification of c-kit⁺Thy-1.1$^{lo}$ Lin$^{-lo}$ Sca-1⁺ Cells c-kit⁺Thy-1.1$^{lo}$Lin$^{-/lo}$Sca-1⁺-staining cells define HSCs. Bone marrow cells were obtained by flushing tibiae and femora 1–5 days after initiation of hydroxyurea treatment. Thy-1.1$^{lo}$Lin$^{-/lo}$Sca-1⁺ cells were stained and isolated from bone marrow as described previously in Spangrude et al. (1988) Science 241:58–62, with the following modifications. The following lineage marker antibodies were used: RAE-6B2 for the B lineage marker B220; RM.-5 (CD2), GK. 1.5 (CD4), 53–7.3 (CD5) and 53.6.72 (CD8) for T cell markers; RB6-8C5 (GR-1) and M1/70.15.11.5 (Mac-1) for myelomonocytic markers; and TER-119 for erythrocytes. Lineage staining were usually revealed with phycoerythrin-conjugated polyclonal anti-rat antibody (Caltag, South San Francisco, Calif.). In some cases, phycoerthrin-conjugated 145-2C11 (CD3) mAb was also added. The cells were stained with biotinylated Sca-1 and were positively selected for Sca-1+ cells using the MACS magnetic bead system (Miltenyl Biotec, Auburn, Calif.). The positive selected cells were further stained with fluorescein conjugated-19XE5 (Thy-1.1), and allophycocyanin conjugated-2B8 (c-kit), and steptavidin-Texas Red. The cells were incubated for 20 minutes on ice for each step. After the final wash, cells were resuspended in PBS containing 1 $\mu$g/ml propidium iodide. The labeled cells were analyzed and sorted with a dual laser FACS® (Becton Dickinson Immunocytometry Systems, Mountain View, Calif.). Dead cells were excluded from analysis by their propidium iodide staining characteristics. After sorting, the purity of c-kit⁺Thy-1.1$^{lo}$Lin$^{-/lo}$Sca-1⁺ cells was checked by reanalysis by FACS®.

Rhodamine 123 and Hoechst 33342 Staining

The staining procedure for Rhodamine 123 (Rh123) is as follows: A 1 mg/ml stock solution of Rh123 (Molecular Probes, Eugene, Oreg.) was prepared in ethanol and stored at −20° C. in the dark just before use. The sorted c-kit⁺Thy-1.1$^{lo}$Lin$^{-/lo}$Sca-1⁺ cells were resuspended at 10⁶/ml or less in BSS buffer containing 2% fetal calf serum (FCS), and incubated with 0.2 $\mu$g/ml of Rh123 dye for 30 min at 37° C. The cells were washed, centrifuged and incubated at 37° C. with 10 $\mu$M Hoechst 33342 (Molecular Probes, Eugene, Oreg.) for 40–60 min to allow DNA labeling of the Hoechst dye and efflux of the Rh123 dye simultaneously. The fluorescence intensity of Rh123 was analyzed by flow cytometry in the fluorescein isothiocyanate (FITC) channel after setting compensation between FITC and phycoerythrin (PE) channels. See FIG. 7 for results of staining analyses of cell cycle.

Long-term Reconstitution Assays

This assay directly measures cells with reconstitution activity in recipients. Recipient mice were lethally irradiated to a total level of 1.1 Grey in two split doses with a 3 hour interval. The sorted bone marrow subset cells were injected (100 $\mu$l/mouse) intravenously into the retro-orbital plexus of anesthetized mice.

To prepare cells for competitive reconstitution assay, BM cells from non-irradiated host congenic strain were harvested and plated into 96-well plate with 120 $\mu$l of cells at concentration of 10⁶ cells /ml. The c-kit⁺Thy-1.1$^{lo}$Lin$^{-/}$$_{lo}$Sca-1⁺ cells/or subsets of these cells were sorted and deposited at 1–120 cells/well by an automated cell deposition unit (ACDU) into these 96-well plates containing the host congenic BM cells. The recipient mice were injected i.v. with 100 $\mu$l of 1–100 c-kit⁺Thy-1.1$^{lo}$Lin$^{-/lo}$Sca-1⁺ cells/or subsets along with 10⁵ host congenic bone marrow harvested from 96-well plates.

Peripheral Blood Analysis for Long-term Reconstitution

Peripheral blood was obtained once every four weeks from the retro-orbital sinus, and red blood cells were lysed prior to mAb staining. Immunofluorescence staining and FACS® analyses were performed as described in Spangrude et al. (1988) Science 241:58–622. Four color immunofluorescence staining was carried out using monoclonal antibodies specific for lineage markers for B cells (anti-B220), myeloid cells (anti-Gr-1 and anti-Mac-1), T cells (anti-CD3, antibody 2C11) cells along with allelic markers specific for donor hematopoietic cells (anti-Ly-5.2, antibody ALI-4A2 or anti-Ly5.1, antibody A20.1).

RESULTS

The normal percentage of HSCs in S/G2/M phases of the cell cycle is pproximately 6–25%; of the so-called "long-term HSC", i.e. the subset exclusively responsible for sustained multilineage equivalent and exclusive HSC self-renewal, the percentage in S/G2/M is only ~1–5%.

FIG. 1 shows the percentage of HSCs in active cell cycle in the bone marrow (BM) and in the periphery following mobilization with the cytokine, G-CSF, and/or chemotherapeutic agents. With cytokine treatment, there are virtually no HSCs in cycle in the peripheral blood (mouse MPB, FIG. 1, panels C and E; human MPB, FIG. 1, panels D and E) in contrast to normal BM (mouse BM, FIG. 1, panel A; human BM, FIG. 1, panel B) where the percentage of cycling cells are already low. FIG. 2 shows that the percentage of HSCs in BM can be increased by treatment with a cell cycle blocker such as hydroxyurea (FIG. 2, panel A versus panel B). In addition, HU treatment also induces and/or accumulates mobilized peripheral HSC into the mitotic cycle (FIG. 2, panel C versus panel D). Table 1 summarizes total number of HSCs and percentage of actively cycling (i.e. S/G2/M) HSCs in long bones of mice treated with PBS (control) or with hydroxyurea for 3 days. As is evident from Table 1, in vivo treatment with HU results in an increase over the PBS treated control, in the number and significantly, the percentage of HSCs in the bone marrow and the percentage of HSCs in S/G2/M phases. This enrichment for HSCs in general can be exploited in bone marrow transplantation.

FIG. 3 shows multilineage reconstitution from transplanting purified c-kit⁺Thy-1.1$^{lo}$Lin$^{-/lo}$Sca-1⁺ (KTLS) cells isolated from mice treated with 100 mg/kg/day of HU for 3 days prior to isolation of KTLS stem cells. One group of lethally irradiated recipient mice were transplanted by injection with ten Ly-5 marked KTLS cells along with 1×10⁵ host type BM cells. The upper 3 panels show data from a representative mouse analyzed at week 24. A second group of mice were injected with 50 S/G2/M phase, Rh123$^{mid}$ KTLS. The lower panels show data from a representative mouse analyzed at week 16. Peripheral blood cells were analyzed as indicated after irradiation and transplantation. The percentages of Ly-5 marked Mac-1⁺Gr-1⁺, B220⁺ or CD3⁺ cells originating from transplanted KTLS cells in a representative mice are indicated in each panel.

Figure 4:
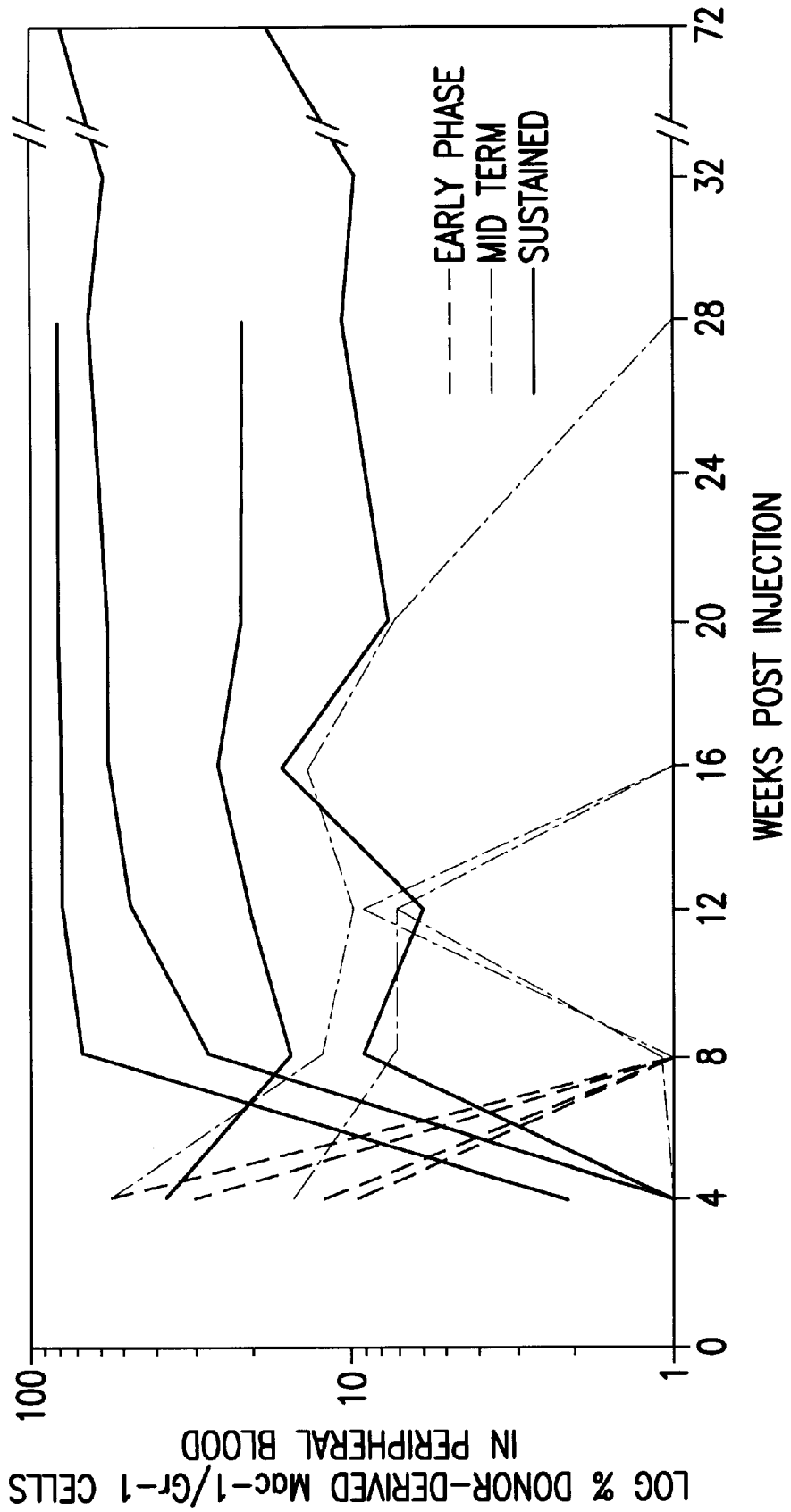
FIG. 4 shows an exemplary productive lifespan of individual Thy-1.1$^{lo}$Lin$^{-/lo}$Sca-1$^+$ HSCs in a normal, non-HU treated mice. Long term and transient reconstitution of donor marked stem cells can be detected by following the fate of Mac-1/Gr-1 cells in peripheral blood.

FIG. 4 exemplifies the productive lifespan of individual Thy-1.1$^{lo}$Lin$^{-/lo}$Sca-1⁺ in a normal, non-HU treated mice.

The assay was performed as described in Uchida, N. "Characterization of mouse hematopoietic stem cells" in doctoral dissertation, Stanford University, 1992. FIG. 4 shows that long term and transient reconstitution of donor marked stem cells can be detected by following the fate of Mac-1/Gr-1 cells in peripheral blood.

Figure 5A:
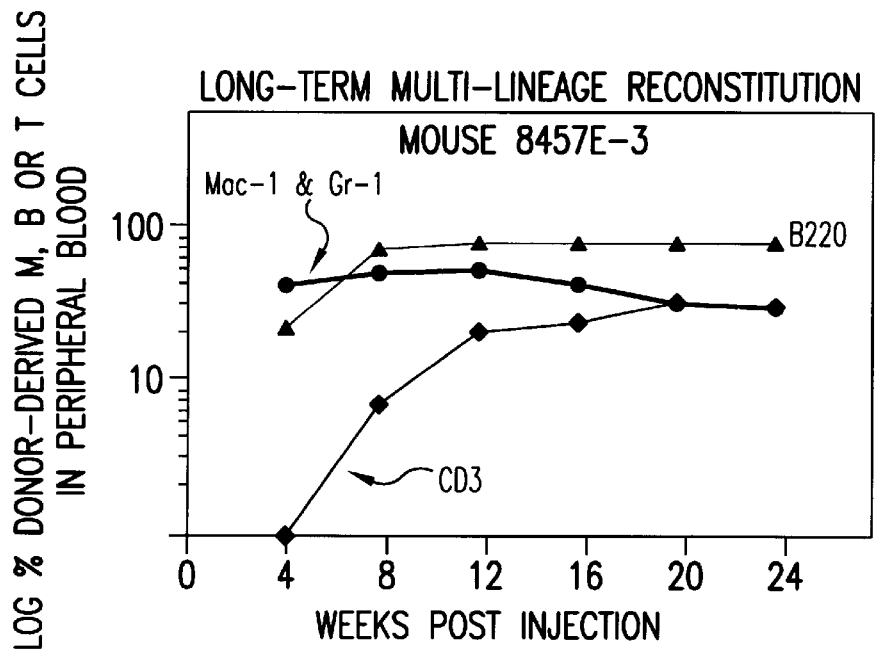
FIG. 5A and FIG. 5B show the productive lifespan in vivo of donor-marked Thy-1.1$^{lo}$Lin$^{-/lo}$Sca-1$^+$ (KTLS) HSCs isolated from HU-treated mice. Graphs show a competitive reconstitution assay with 10 HU-treated KTLS cells (Ly-5.2)+10$^5$ normal bone marrow cells (Ly5.1)
Figure 5B:
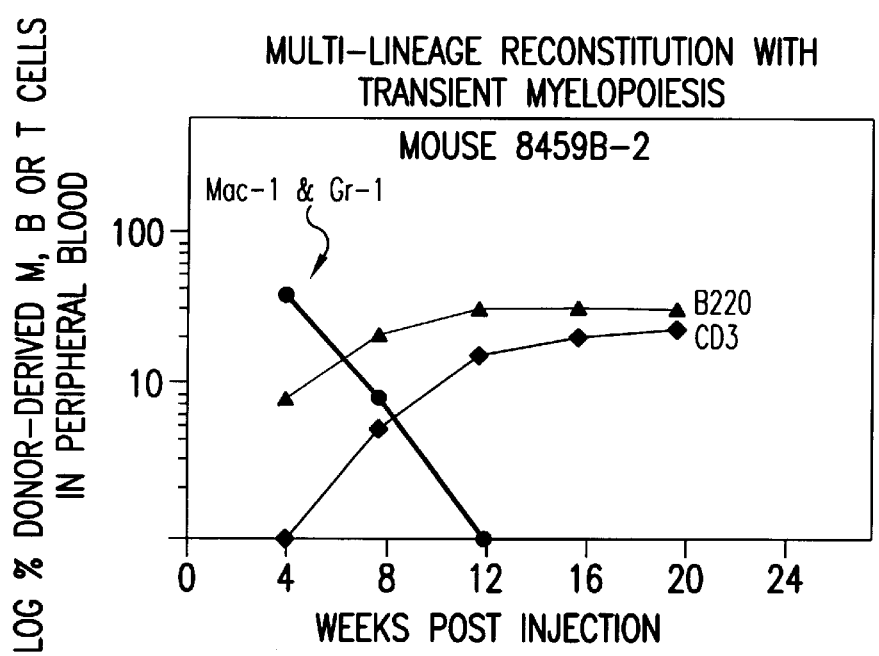

FIG. 5 shows the productive lifespan of donor marked KTLS HSCs in vivo, the HSCs being isolated from HU-treated mice. Mice were treated with HU as described above. The long term and transient multi-lineage reconstitution in an individual mouse is shown in FIGS. 5A and 5B, respectively. FIG. 5A from representative mouse 8457E-3, shows long term reconstitution of B (B220), T (CD3) and monogranulocytic lineages (Mac-1 & Gr-1). The 8459B-2 representative mouse shows transient reconstitution of monocyte and granulocyte lineages as analyzed by staining for Mac-1 and Gr-1 cell surface markers. As can be seen from the figure, thorough analysis for long term reconstitution should include the analysis of monocytic and granulocytic lineages since usually B cells (B220) and T cells (CD3) will show long term reconstitution.

Figure 6A:
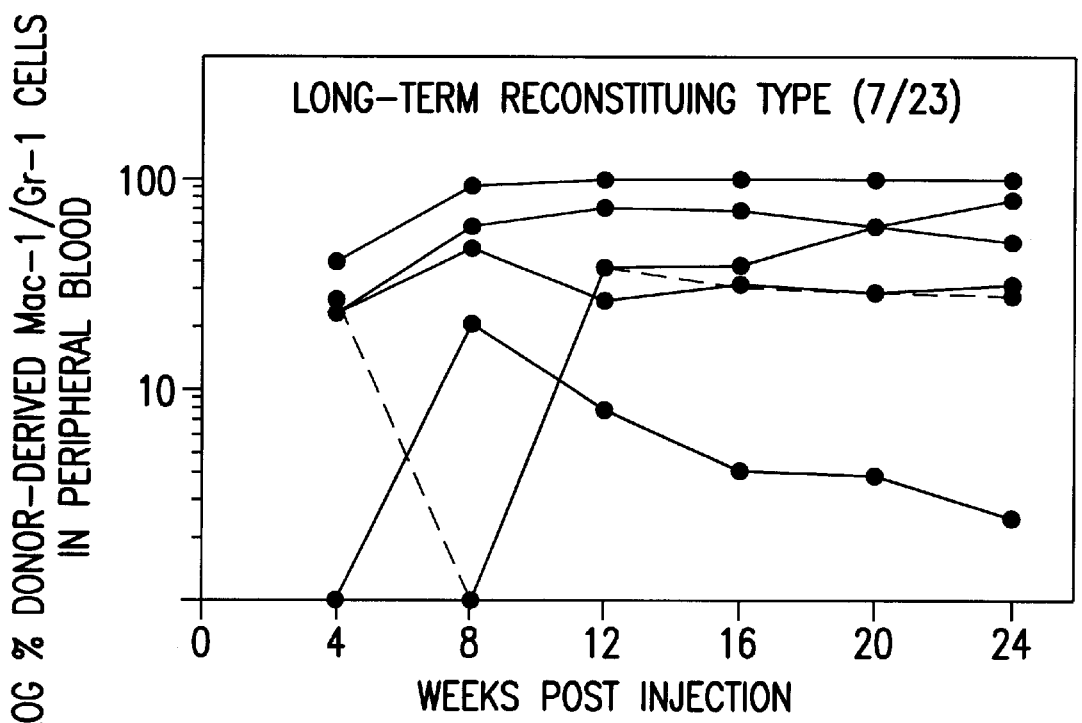
FIGS. 6A and FIG. 6B show two representative examples of how stem cell clones reconstitute a lethally irradiated mouse in a competitive assay as described herein. Both long-term multilineage reconstitution (FIG. 6A) and multi-lineage reconstitution with transient myelopoiesis (FIG. 6A) are shown. In long-term reconstitution, myeloid cells (Mac-1 & Gr-1) are sustained in peripheral blood or do not disappear.
Figure 6B:
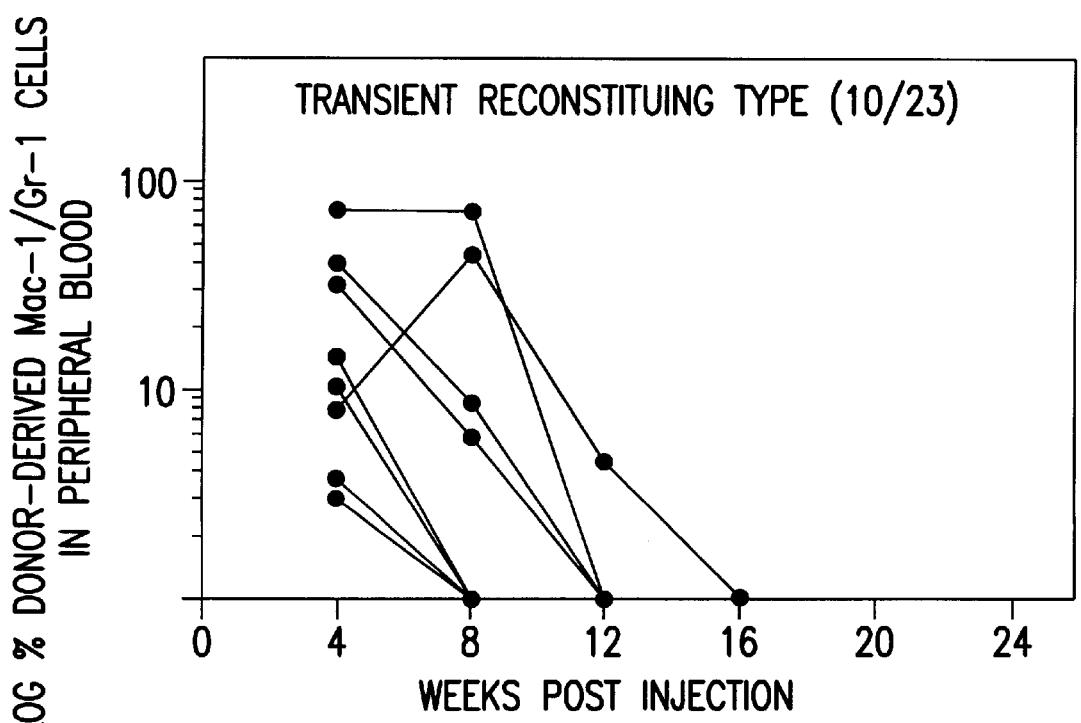

FIG. 6 shows the productive lifespan in vivo of donor-marked $c\text{-}kit^+Thy\text{-}1.1^{lo}Lin^{-/lo}Sca\text{-}1^+$ (KTLS) HSCs isolated from mice treated with HU at about 100 mg/kg/body weight per day, as analyzed by competitive reconstitution assay. Ten HU-treated KTLS cells (Ly-5.2) were transplanted with $10^5$ normal BM cells. The recipient mice were analyzed up to 24 weeks. Of the 23 animals analyzed, 10/23 showed transient multilineage of myeloid and 7/23 showed sustained (up to 24 weeks) multilineage reconstitution (FIG. 6B and FIG. 6A, respectively). As can be seen by comparison with FIG. 4, the reconstitition profile of HU treated HSCs is relatively analagous to the reconstitution profile by stem cells from normal, non-HU treated mice.

Figure 7:
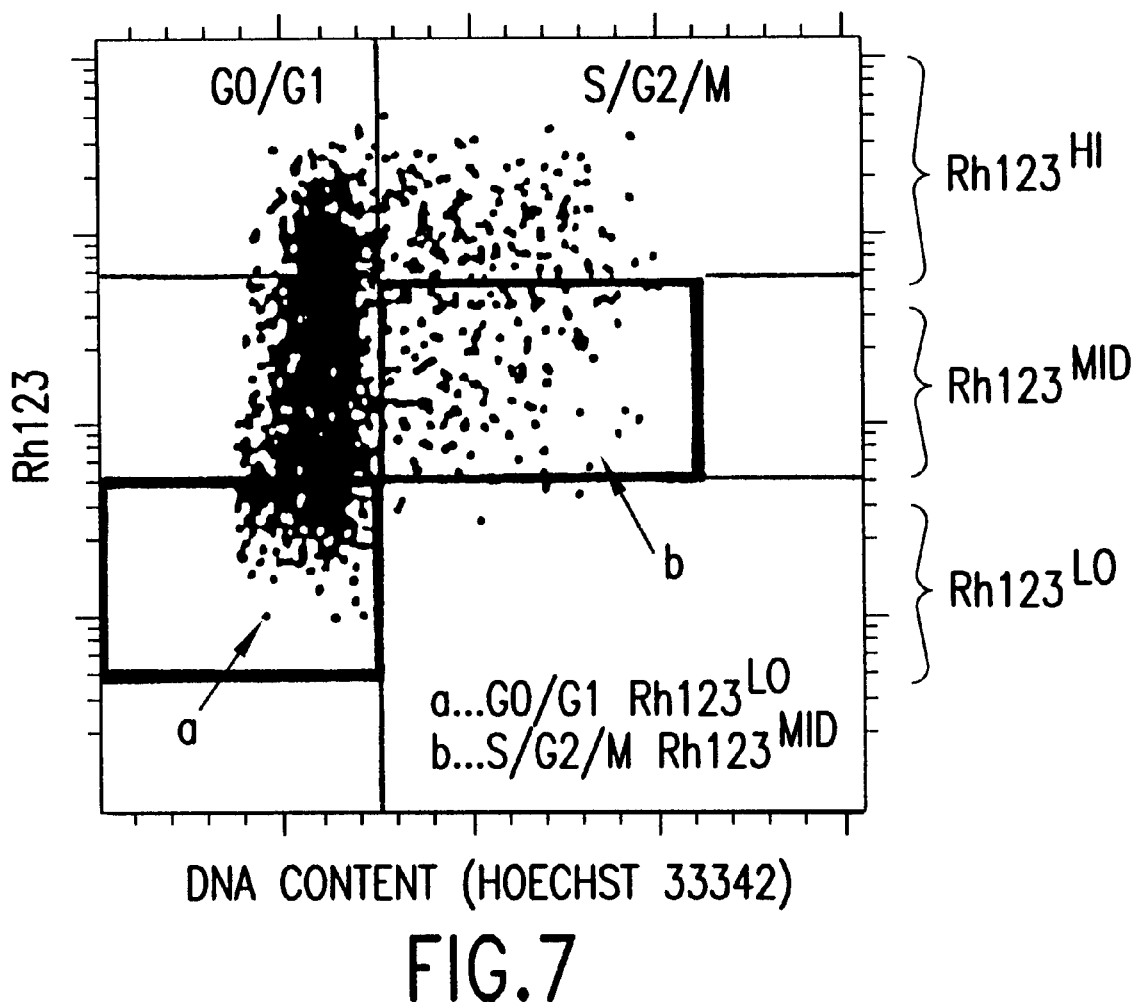
FIG. 7 is a FACS plot showing the cell cycle status of KTLS HSCs isolated from hydroxyurea treated mouse bone marrow, as indicated by rhodamine (Rho123) and Hoechst 33342 staining.

The cell cycle status of HSCs can be determined by rhodamine (Rh123) staining and staining for DNA content with Hoechst 33342. As shown in FIG. 7, $Rh123^{lowest}$ ($Rh^{lo}$) KTLS cells tend to be in G0/G1 (see G0/G1, $Rh123^{lo}$). Some cells in S/G2/M phases have the ability to efflux $Rho^{123}$ dye (see S/G2/M $Rh123^{mid}$).

TABLE 2

Contributions of G0/G1 $Rh123^{lo}$ and S/G2/M $Rh123^{mid}$ subsets of marked $c\text{-}kit^+$ Thy-1.1$^{lo}$ Lin$^{-/lo}$ Sca-1$^+$ (KTLS) from hydroxyurea treated mice to blood cell production

| KTLS subset | Transient & long-term (1/frequency) | CI** | LTMR* only (1/frequency) | CI |
|---|---|---|---|---|
| KTLS | 4.1 | 2.7–8.9 | 29.2 | 21.5–45.3 |
| G0/G1 Rh123$^{lo}$ | 4.1 | 3.0–6.5 | 20.3 | 14.1–35.8 |
| S/G2/M Rh123$^{mid}$ | 6.2 | 4.0–13.6 | 66.7 | 36.9–350.8 |

The frequency of donor KTLS subsets contributing to blood cell production in a competitive reconstitution assay (as described above) was calculated based on linear regression analysis, by SAS program.
*PLTMR = long term multilineage reconstitution
**CI = confidence interval (lower bound 95% – upper bound 95%)

All publications and patent documents cited herein are incorporated by reference in their entirety as if each individual publication or patent document was specifically and individually indicated to be incorporated by reference.

The particular embodiments described above are provided by way of illustration and are not meant to be construed as a limitation on the scope of the invention. It will be apparent to one of ordinary skill in the art that many modifications can be made to the present invention without departing from the spirit or essential characteristics of the invention.

What is claimed is:

1. A method of generating transduced hematopoietic stem cells (HSCS) of a mammal, comprising
    (a) contacting HSCs of a mammal in vivo with an amount of hydroxyurea effective to increase the number of actively cycling HSCs by at least 1.5 fold, said effective amount being administered in a dosage range of 10 mg to 200 mg/kg body weight per day;
    (b) removing the HSCs of step (a) from the mammal; and
    (c) introducing a gene into the HSCs of step (b) ex vivo using retroviral mediated gene transfer,
    thereby generating an increase in the number of transduced HSCs over that in the absence of contact with hydroxyurea.

TABLE 1

Numbers of HSCs and % HSCs in S/G2/M phases recovered after treating mice with continuous PBS pump or hydroxyurea (HU) by continuous infusion.

| Analysis Date | Treatment (/kg) | Length of treatment (days) | BM cell numbers | % HSCs | Numbers of HSCs | % HSCs in S/G2/M |
|---|---|---|---|---|---|---|
| 11/13/95 | PBS pump | 3 | 2.6 × 10$^7$ | 0.16 | 4.3 × 10$^4$ | 8.6 |
|  | HU 50 mg | 3 | 3.4 × 10$^7$ | 0.21 | 7.2 × 10$^4$ | 16.9 |
| 11/15/96 | PBS pump | 5 | 2.4 × 10$^7$ | 0.066 | 1.6 × 10$^4$ | 1.8 |
|  | HU 50 mg | 5 | 3.3 × 10$^7$ | 0.146 | 7.2 × 10$^4$ | 5.8 |
| 11/30/95 | PBS pump | 3 | 3.1 × 10$^7$ | 0.039 | 1.2 × 10$^4$ | 7.8 |
|  | HU 100 mg | 3 | 8.4 × 10$^6$ | 0.261 | 2.2 × 10$^4$ | 22.9 |
| 12/11/95 | PBS pump | 3 | 2.4 × 10$^7$ | N/A | N/A | 5.6 |
|  | HU 100 mg | 3 | 1.3 × 10$^7$ | N/A | N/A | 22.0 |
| 12/18/95 | PBS pump | 3 | 2.1 × 10$^7$ | N/A | N/A | N/A |
|  | HU 100 mg | 3 | 1.9 × 10$^7$ | N/A | N/A | 14.9 |
| 1/8/96 | PBS pump | 3 | 4.3 × 10$^7$ | 0.064 | 2.7 × 10$^4$ | N/A |
|  | HU 100 mg | 3 | 1.8 × 10$^7$ | 0.36 | 6.4 × 10$^4$ | 19.6 |
| AVERAGE | PBS pump | 3 | 2.9 ± 0.86 × 10$^7$ | 0.09 ± 0.07 | 2.73 ± 1.55 × 10$^4$ | 7.34 ± 1.56 |
|  | HU 100 mg | 3 | 1.46 ± 0.49 × 10$^7$ | 0.31 ± 0.07 | 4.30 ± 1.55 × 10$^4$ | 19.6 ± 3.41 |

BM cells were harvested from four long bones from each mouse. In each experiment, about 3–10 mice per group were pooled to generate the data above. HSCs were defined as $c\text{-}kit^+$ Thy-1.1$^{lo}$ Lin$^{-/lo}$ Sca-1$^+$. N/A, not available.

2. A method of generating transduced hematopoietic stem cells (HSCs) of a mammal, comprising:
   (a) contacting HSCs with an amount of hydroxyurea effective to increase the number of actively cycling HSCs by at least 1.5 fold, wherein the contacting is done ex vivo; and
   (b) introducing a gene into the HSCs of step (a) ex vivo using retroviral mediated gene transfer, thereby generating an increase in the number of transduced HSCs over that in the absence of contact with hydroxyurea.

3. The method of claim 1, wherein the effective amount is administered to a mammalian subject in a dosage range of 50 mg to 150 mg/kg body weight per day prior to gene transfer.

4. The method of claim 1, wherein the gene is a therapeutic gene.

5. A method of increasing the number of HSCs available for bone marrow transplantation by administering to a bone marrow donor an amount of hydroxyurea effective to increase the number of HSCs available for bone marrow transplantation by at least 1.5 fold, prior to stem cell harvest from the donor, said effective amount being administered in a dosage range of 10 mg to 200 mg/kg body weight per day.

6. The method of claim 3 wherein the hydroxyurea is administered to the subject orally or intravenously.

7. The method of claim 3 wherein the hydroxyurea is administered to the subject for 3 to 7 consecutive days.

8. The method of claim 5 wherein the hydroxyurea is administered to the bone marrow donor orally or intravenously.

9. The method of claim 5 wherein the hydroxyurea is administered to the donor in a dosage range of 50 mg to 150 mg/kg body weight per day.

* * * * *